(12) United States Patent
Chow

(10) Patent No.: US 8,175,706 B2
(45) Date of Patent: May 8, 2012

(54) OVERLAPPING PACING AND TACHYARRHYTHMIA DETECTION ZONES

(75) Inventor: Theodore Chow, Saratoga, CA (US)

(73) Assignee: Medtronic, Inc., Minneapolis, MN (US)

( * ) Notice: Subject to any disclaimer, the term of this patent is extended or adjusted under 35 U.S.C. 154(b) by 290 days.

(21) Appl. No.: 12/494,038

(22) Filed: Jun. 29, 2009

(65) Prior Publication Data

US 2010/0057156 A1    Mar. 4, 2010

Related U.S. Application Data

(60) Provisional application No. 61/190,905, filed on Sep. 4, 2008.

(51) Int. Cl.
*A61N 1/00* (2006.01)
(52) U.S. Cl. .......................................................... 607/14
(58) Field of Classification Search .................. 607/4, 9, 607/14, 15, 16, 17, 19, 20, 31
See application file for complete search history.

(56) References Cited

U.S. PATENT DOCUMENTS

| | | | |
|---|---|---|---|
| 5,243,980 A | 9/1993 | Mehra | |
| 5,370,667 A | 12/1994 | Alt | |
| 5,458,622 A | 10/1995 | Alt | |
| 5,609,613 A * | 3/1997 | Woodson et al. ............... | 607/19 |
| 5,882,352 A | 3/1999 | Duncan et al. | |
| 6,230,055 B1 | 5/2001 | Sun et al. | |
| 6,445,949 B1 | 9/2002 | Kroll | |
| 6,636,764 B1 | 10/2003 | Fain et al. | |
| 6,978,177 B1 | 12/2005 | Chen et al. | |
| 7,120,491 B1 | 10/2006 | Bailin et al. | |
| 2004/0127943 A1 | 7/2004 | Henry et al. | |
| 2008/0045851 A1 | 2/2008 | Cazares et al. | |

FOREIGN PATENT DOCUMENTS

| | | |
|---|---|---|
| EP | 0253505 A2 | 1/1988 |
| WO | 0038782 A1 | 7/2000 |

OTHER PUBLICATIONS

Reply to Written Opinion from corresponding PCT Application Serial No. PCT/US2009/056109 dated Dec. 9, 2010 (12 pgs.).
International Search Report and Written Opinion for PCT/US2009/056109, dated Sep. 9, 2010, 13 pages.
International Preliminary Report on Patentability from corresponding PCT Application Serial No. PCT/US2009/056109 dated Jan. 18, 2011 (11 pages).
Response to Rule 161(1) EPC communication from counterpart European Patent Application No. 09807521.1 dated Jan. 18, 2012 (9 pages).

* cited by examiner

*Primary Examiner* — George Manuel
*Assistant Examiner* — Robert Wieland
(74) *Attorney, Agent, or Firm* — Shumaker & Sieffert, P.A.

(57) ABSTRACT

An example implantable medical device (IMD), such as an implantable cardioverter defibrillator, may be configured to store a ventricular tachycardia zone, wherein the ventricular tachycardia zone specifies ventricular depolarization rates indicative of ventricular tachycardia, and to deliver pacing pulses to at least one ventricle of a heart in response to detecting intrinsic atrial depolarizations at rates within the ventricular tachycardia zone. The IMD may further store a maximum ventricular tracking rate that is greater than a lower bound of the ventricular tachycardia zone, and be further configured to deliver the pacing pulses to the at least one ventricle in response to detecting intrinsic atrial depolarizations at rates up to the maximum ventricular rate. In this manner, the IMD may be configured with overlapping pacing and tachyarrhythmia detection zones. In some examples, the IMD dynamically modifies the maximum ventricular tracking rate for ventricular tracking pacing within the ventricular tachycardia zone.

37 Claims, 13 Drawing Sheets

OVERLAPPING PACING AND TACHYARRHYTHMIA DETECTION ZONES

This application claims the benefit of U.S. Provisional Application No. 61/190,905, filed Sep. 4, 2008, which is hereby incorporated by reference in its entirety.

TECHNICAL FIELD

This disclosure relates to implantable medical devices and, more particularly, implantable medical devices that deliver cardiac therapy.

BACKGROUND

Cardiac pacing is delivered to patients to treat a wide variety of cardiac dysfunctions. Cardiac pacing is often delivered by an implantable medical device (IMD), which may also be equipped to provide cardioversion or defibrillation, if needed. The IMD delivers such stimulation to the heart via electrodes located on one or more leads, which are typically intracardiac leads.

In demand pacing, a pacing pulse is delivered when an interval expires without detecting an intrinsic depolarization of the heart. The interval may be referred to as an escape interval, and controls the minimum rate of depolarizations. In rate-responsive pacing, the escape interval may be varied based on the physiological needs of the patient, as indicated by one or more sensors. As an example, an activity or respiration sensor may indicate increased exertion or activity of the patient, which in turn indicates a need for an increased heart rate and shortening of the escape interval. The depolarization rate indicated by the output of the one or more sensors may be referred to as a sensor-indicated rate.

In cases in which a patient's atrioventricular conduction is compromised, the ventricular pacing may be delivered an atrioventricular (A-V) interval after detection of an intrinsic or paced atrial depolarization. The A-V interval may also be varied based on the output of the rate-response sensor(s). Such pacing of the ventricles may be referred to as ventricular tracking pacing, because the paced depolarizations of the ventricles track the rate of depolarizations of the atria.

Patients with heart failure are, in some cases, treated with cardiac resynchronization therapy (CRT). CRT is a form of cardiac pacing. In some examples, CRT involves delivery of pacing pulses to both ventricles to synchronize their contraction. In other examples, CRT involves delivery of pacing pulses to one ventricle to synchronize its contraction with that of the other ventricular, such as pacing the left ventricle to synchronize its contraction with that of the right ventricle.

Ventricular tachycardia (VT) and ventricular fibrillation (VF) are cardiac arrhythmias that originate in the ventricles of the heart. The ventricular rate during VT may range from 150 beats per minute (bpm) to 188 bpm, for example, and is relatively stable. The ventricular rate during VF is more rapid, and may be unstable or disorganized. VT may be treated by anti-tachycardia therapies, such as anti-tachycardia pacing or cardioversion. VF may be treated with defibrillation. Supraventricular tachycardia (SVT) is characterized by a rapid ventricular rate (e.g., 150 bpm to 188 bpm), but originates from outside of the ventricles, e.g., the atria or the atrioventricular node. In some cases, SVT does not require treatment.

Conventional IMDs for treating ventricular tachyarrhythmias, such as VT or VF, monitor the ventricular rate and determine whether the ventricular rate falls within one or more zones, e.g., a VT zone and/or a VF zone. An example VT zone is a zone of ventricular rates between and including 150 bpm and 188 bpm. An example VF zone includes rates greater than 188 bpm. Conventional IMDs apply anti-tachycardia therapy or defibrillation when the ventricular rate is within the VT or VF zone for a threshold number of consecutive or proximate depolarizations. Conventional IMDs do not allow a sensor indicated pacing rate to exceed the lower bound of the VT zone, or a ventricular tracking rate to track atrial rates above the lower bound of the VT zone.

SUMMARY

In general, this disclosure describes techniques for configuring an implantable medical device (IMD) to continue to track atrial rates, and thereby pace the ventricles of a patient's heart at rates, that are within a ventricular tachycardia (VT) zone. In this manner, the IMD may pace the heart into the VT zone, but the VT will be of supraventricular origin due to ventricular tracking of the atrial rate. However, when the intrinsic ventricular rate is within the VT zone as a result of ventricular tachycardia, the IMD may deliver an anti-tachycardia therapy.

In general, the VT zone is defined according to a range of ventricular rates, e.g., in beats per minute (bpm). For example, the VT zone may include ventricular rates between and including 150 bpm and 188 bpm. A pacing zone, e.g., within which the sensor indicated rate may vary, may generally include rates below the lower bound of the VT zone, e.g., up to and including 140 bpm. The atria and ventricles may be paced at any sensor indicated rate within the pacing zone.

In accordance with the techniques of this disclosure, the IMD may continue to track intrinsic atrial rates and pace the ventricles up to a maximum ventricular tracking rate that is above the pacing zone and within the VT zone, e.g., 170 bpm. The zone between and including the lower bound of the VT zone and the maximum tracking rate, e.g., between and including 150 bpm and 170 bpm, may comprise an "overlap zone" in which the IMD may both pace the ventricles, and detect VT to deliver an anti-tachycardia therapy, such as cardioversion. In this manner, the IMD may continue to pace the ventricles as if the IMD were in the pacing zone up to 170 bpm when the heart rhythm entered the overlap zone as a result of SVT, but still treat a VT in the overlap zone that is of ventricular origin.

It may be desirable to allow ventricular pacing at rates within a VT zone in a variety of situations. Some patients have relatively slow VTs, but also are physically active, and would benefit from pacing support at rates higher than the slow VTs during physical activity. Additionally, for CRT patients, it is generally desirable that all or substantially all depolarizations are paced so that ventricular activity is synchronized. During an SVT with a rate outside of the pacing zone, a conventional IMD would typically not pace the ventricles. However, efficiency of ventricular contraction may be of increased importance when the diastolic filling period is short during high ventricular rates. Thus, pacing the ventricles of a CRT patient at a high rate, as may be provided in some examples according to this disclosure, may be desirable.

If an IMD according to the disclosure senses one or more ventricular events, e.g., depolarizations, while pacing in the VT zone, the IMD may modify the pacing mode or parameters to suspend or modify pacing in the VT zone. In some examples, the IMD modifies lower the maximum ventricular tracking rate to below the lower bound of the VT zone. The IMD may then apply VT detection to determine whether the rhythm remains in the VT zone, and rhythm discrimination techniques to determine whether the rhythm is a VT or an SVT. When the IMD determines that the rhythm is not sustained or its origin is supraventricular, e.g., from one or both atria or the atrioventricular node, the IMD may reset the maximum ventricular tracking rate and pace the ventricles in the VT zone, if indicated by the atrial rate, even if this pacing occurs while the heart rhythm is in the overlap portion of the VT zone. However, when the IMD determines that the origin of an intrinsic rhythm in the VT zone is the ventricles, the IMD provide responsive therapy for the VT, such as anti-tachycardia pacing, cardioversion or defibrillation.

In one example, a method comprises storing a ventricular tachycardia zone, wherein the ventricular tachycardia zone specifies ventricular depolarization rates indicative of ventricular tachycardia, and delivering ventricular tracking pacing at rates within the ventricular tachycardia zone, wherein delivering ventricular tracking pacing comprises delivering pacing pulses to at least one ventricle of a heart in response to detecting intrinsic atrial depolarizations at rates within the ventricular tachycardia zone.

In another example, a medical system comprises a memory that stores a ventricular tachycardia zone, wherein the ventricular tachycardia zone specifies ventricular depolarization rates indicative of ventricular tachycardia, a medical device that detects intrinsic atrial depolarizations, and a control unit controls the medical device to deliver ventricular tracking pacing at rates within the ventricular tachycardia zone by at least delivering pacing pulses to at least one ventricle of a heart in response to the medical device detecting intrinsic atrial depolarizations at rates within the ventricular tachycardia zone.

In another example, a computer-readable medium is encoded with instructions for causing a programmable processor to store a ventricular tachycardia zone, wherein the ventricular tachycardia zone specifies ventricular depolarization rates indicative of ventricular tachycardia, and control a medical device to deliver ventricular tracking pacing at rates within the ventricular tachycardia zone, wherein the instructions that cause the programmable processor to control the medical device to provide ventricular tracking pacing comprise instructions that cause the programmable processor to control the medical device to deliver pacing pulses to at least one ventricle of a heart in response to detecting intrinsic atrial depolarizations at rates within the ventricular tachycardia zone.

In another example, a medical system comprises means for storing a ventricular tachycardia zone, wherein the ventricular tachycardia zone specifies ventricular depolarization rates indicative of ventricular tachycardia, and means for delivering ventricular tracking pacing at rates within the ventricular tachycardia zone, wherein the means for delivering ventricular tracking pacing comprises means for delivering pacing pulses to at least one ventricle of a heart in response to detecting intrinsic atrial depolarizations at rates within the ventricular tachycardia zone.

The details of one or more examples are set forth in the accompanying drawings and the description below. Other features, objects, and advantages will be apparent from the description and drawings, and from the claims.

DETAILED DESCRIPTION

Figure 1:
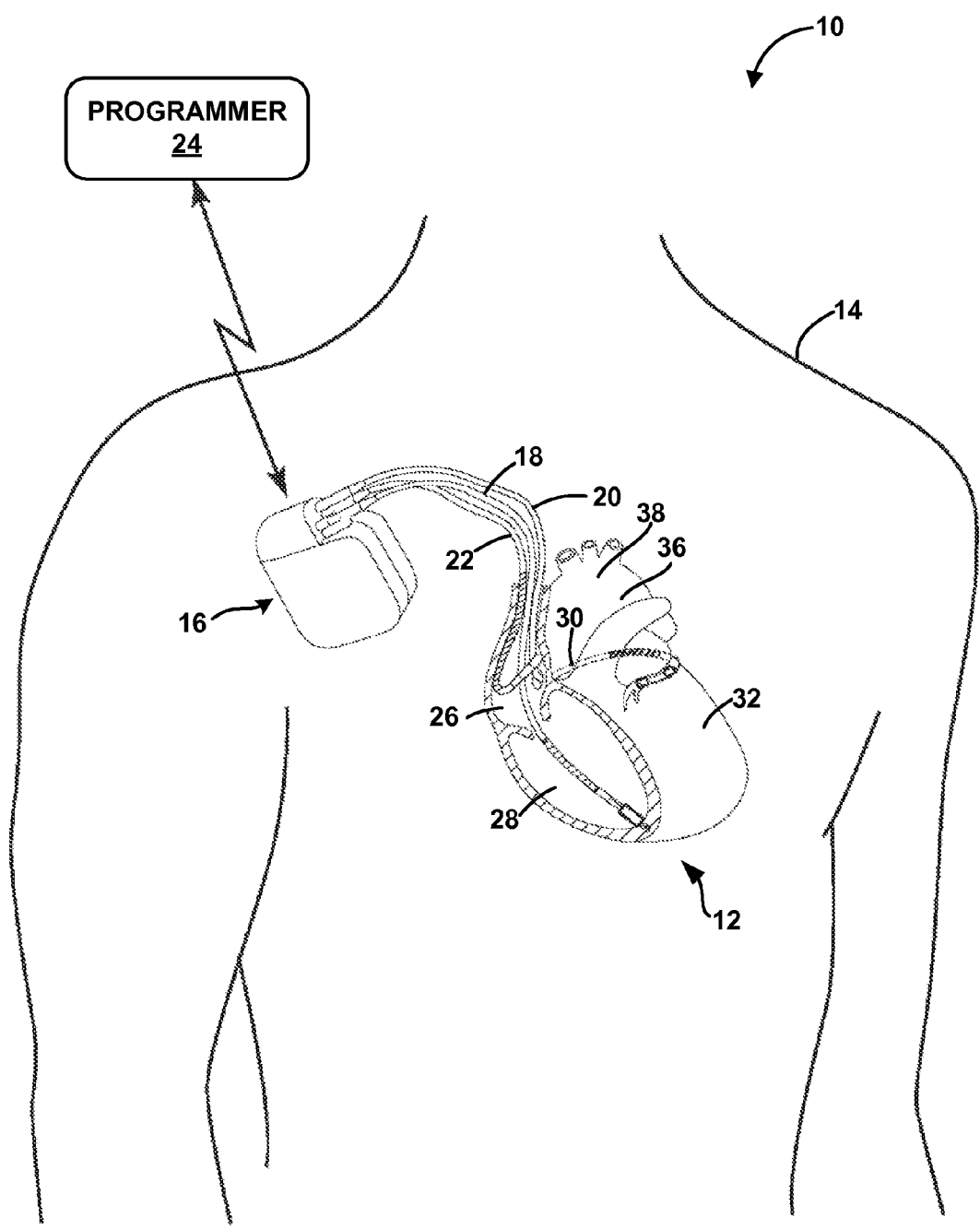
FIG. 1 is a conceptual diagram illustrating an example therapy system that provides cardiac pacing therapy to a heart of a patient.

FIG. 1 is a conceptual diagram illustrating an example therapy system 10 that provides cardiac pacing therapy to a heart 12 of a patient 14. Therapy system 10 includes an IMD 16, which is coupled to leads 18, 20, and 22, and programmer 24. IMD 16 comprises a pacemaker, and may also comprise a cardioverter and/or defibrillator, e.g., an implantable cardioverter defibrillator (ICD). IMD 16 provides pacing signals, and may also provide cardioversion or defibrillation signals, to heart 12 via electrodes coupled to one or more of leads 18, 20, and 22.

IMD 16 may execute the techniques described in this disclosure. IMD 16 may be configured to track atrial rates and pace heart 12 into a ventricular tachycardia (VT) zone. That is, when IMD 16 tracks atrial rates that enter the VT zone, IMD 16 may continue to deliver pacing therapy to one or both of ventricles 28, 32 of heart 12, even when this pacing therapy causes the ventricles to be paced in the VT zone.

While pacing in the VT zone, IMD 16 may monitor ventricles 28, 32 to detect intrinsic ventricular depolarizations. Upon detecting an intrinsic ventricular depolarization, IMD 16 may determine a cause of the intrinsic ventricular depolarization. In one example, IMD 16 is configured with, e.g., programmed with, an overlapping ventricular pacing and ventricular detection/therapy zone, in which an upper ventricular pacing rate is higher during tracking of spontaneous atrial depolarizations than it is following paced atrial depolarizations zone, and in which IMD 16 automatically shifts the upper ventricular tracking rate following a sensed ventricular event (or events). In this manner, IMD 16 may include the ability to detect and treat ventricular tachycardias that may occur during ventricular pacing within the overlap zone. In some examples, IMD 16 may apply a rate smoothing algorithm to prevent a sudden change in heart rate. IMD 16 may also apply rhythm discriminators on a sensed ventricular rhythm in the overlap zone.

In some examples, the rate at which IMD 16 lowers the upper tracking rate in response to sensing one or more ventricular events while delivering ventricular tracking pacing in the overlap zone is proportional to the number of sensed ventricular events that are detected. Likewise, in some examples, the amount by or value to which IMD 16 drops the upper tracking rate following one or more sensed ventricular events is proportional to the number of ventricular events that are sensed. In this manner, IMD 16 may drop the upper tracking rate more quickly or by a greater amount, depending on the number of sensed ventricular events.

In some examples, IMD 16 determines the rate to which to drop the tracking rate following two consecutive sensed ventricular events during ventricular tracking pacing in the overlap zone based on a determined interval between the two events. That is, during a first beat, IMD 16 may sense a first ventricular event, and during a second beat immediately following the first beat, IMD 16 may sense a second ventricular event. IMD 16 may then determine a time interval between the first sensed event and the second sensed event, and determine an amount by which to reduce the upper tracking rate based on the interval. For example, when IMD 16 determines that the interval between the first sensed event and the second sensed event is 350 milliseconds (ms), IMD 16 may set the upper tracking rate interval to 360 ms.

In some examples, IMD 16 waits a period of time after a sensed ventricular event before dropping the upper tracking rate. The period of time may be determined based on input from one or more physiological sensors, such as a pressure sensor, flow sensor, or other sensors that generate a signal that varies based on patient hemodynamic and/or vital status. In some examples, IMD 16 determines the amount by which to reduce the upper tracking rate after a sensed ventricular event based on input from one or more physiological sensors, such as a pressure sensor, flow sensor, or other sensors that generate a signal that varies based on patient hemodynamic and/or vital status.

In some examples, IMD 16 may analyze a morphology of one or more ventricular events sensed while pacing the ventricles in the overlap zone, and the morphology may affect the programmed algorithm response. In some examples, when IMD 16 determines that the morphology is consistent with atrial premature contraction, IMD 16 may provide one response, but when IMD 16 determines that the morphology is consistent with a beat of ventricular origin, IMD 16 may provide a different response. For example, IMD 16 may lower the upper tracking rate to a first rate if the morphology of the sensed ventricular event is consistent with a ventricular origin, and lower the upper tracking rate to a second, higher rate, or not lower the upper tracking rate at all, if the morphology of the sensed ventricular event is consistent with a supraventricular origin. In this manner, the morphology of the sensed ventricular event may affect the programmed algorithm response, e.g., affect the upper ventricular tracking rate.

In some examples, after sensing a first ventricular event, IMD 16 starts a timer of a predetermined duration, and reduces the upper ventricular tracking rate. If IMD 16 determines that the timer expires before sensing a second event, IMD 16 begins increasing the upper tracking rate. In this manner, IMD 16 may minimize the affect of a single ectopic beat on overall heart rate stability.

In some examples, IMD 16 provides a ventricular hysteresis feature for the overlap zone. For example, following a sensed ventricular event during ventricular tracking pacing in the overlap zone, IMD 16 may inhibit ventricular tracking pacing, e.g., by reducing the upper tracking rate for a prescribed period of time, which may correspond to the length of a single cardiac cycle. At the end of the prescribed time, IMD 16 may utilize the upper tracking rate used before the sensed ventricular event. However, if IMD 16 senses a second ventricular event prior to expiration of a timer programmed with the prescribed time after the first sensed event, IMD 16 may reset a timer and apply VT/SVT discriminators to the sensed rhythm. IMD 16 may continue to attempt to sense ventricular events, such that continued sensing would be required to have the VT discrimination algorithm applied. IMD 16 may therefore effectively drop the upper tracking rate as long as IMD 16 continues to sense ventricular events.

In some examples, IMD 16 includes an activity sensor, such as an accelerometer. In some examples, IMD 16 provides ventricular tracking pacing in the overlap zone only when the activity sensor indicates that patient 14 is exercising or otherwise adequately active. A clinician may utilize programmer 24 to configure an activity threshold at which the activity sensor indicates that patient 14 is active or exercising. In this manner, the activity threshold for triggering the overlap zone may be a programmable feature of IMD 16.

In some examples, IMD 16 determines the upper ventricular tracking rate based on the activity level or state of the patient determined based on the output of the activity sensor. In such examples, more intense activity or exercise generally relates to a higher overlap zone upper heart rate. A clinician may utilize programmer 24 to program the relationship between the activity level and the upper heart rate of the overlap zone. Programmable aspects of the relationship between exercise intensity and upper heart rate in the overlap zone may include absolute upper tracking rate, activity slope (the amount by which to increase the upper tracking rate per a unit of increase in activity), and an activity threshold (activity level above which IMD 16 increases the upper tracking rate of the overlap zone).

In general, a clinician may utilize programmer 24 or any other computing device to configure any of the thresholds, upper ventricular tracking rate values, relationships between upper tracking values and other values, time limits, periods, or intervals, or any other values described herein.

Leads 18, 20, 22 extend into the heart 12 of patient 16, and include electrodes (not shown) to sense electrical activity of heart 12 and deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, IMD 16 delivers pacing pulses to one or more the chambers of heart 12 based on the sensed electrical signals in such a manner as to provide cardiac resynchronization therapy (CRT) for patient 14. For CRT, IMD 16 delivers pacing pulses to the left ventricle, and may also deliver pacing pulses to the right ventricle, of heart 12. The delivery of pacing pulses to the ventricles may be timed according to an atrio-ventricular interval (A-V interval), corresponding to a time period following an intrinsic or paced depolarization of an atrium, e.g., the right atrium, after which to apply a ventricular pacing pulse. In some examples, the delivery of a pacing pulse to the left ventricle is timed from an intrinsic or paced depolarization of the right ventricle.

In accordance with the techniques of this disclosure, IMD 16 may provide for overlapping zones for ventricular pacing and ventricular tachycardia (VT) detection. That is, IMD 16 may provide ventricular pacing even when such pacing causes the ventricles to enter a VT zone. IMD 16 may be configured with several heart rhythm "zones." For example, IMD 16 may be configured with a pacing zone including a heart rhythm between 60 beats per minute and 140 beats per minute, a VT zone including a heart rhythm between 150 beats per minute and 188 beats per minute, and a ventricle fibrillation (VF) zone including a heart rhythm above 188 beats per minute. IMD 16 may further be configured with an overlapping zone between the pacing zone and the VT zone, where the overlapping portion of these two zones may include, for example, a heart rhythm range between 140 beats per minute and 170 beats per minute. In this manner, IMD 16 may be configured with an overlap of a pacing rate zone and a VT detection zone. IMD 16 may pace RV 28 and/or LV 32 in the overlap zone, corresponding to a portion of the VT detection zone. In this example, the upper sensor rate for the pacing zone is 140 bpm, but IMD 16 may perform ventricular tracking pacing up to 170 bpm, which corresponds to an upper ventricular tracking rate.

In general, IMD 16 may perform rate responsive pacing in the pacing zone. In one example, IMD 16 performs rate responsive pacing up to a heart rhythm of 140 bpm. However, using the overlap zone, IMD 16 may perform ventricular tracking of native atrial activity up to a rate of 170 bpm, e.g., to accommodate physiological causes of sinus tachycardia, such as exercise. In this manner, IMD 16 may perform ventricular pacing during atrial tracking up to a predetermined maximum tracking rate, such as 170 bpm. This disclosure also refers to the maximum tracking rate as an "upper" tracking rate. Accordingly, IMD 16 may pace the ventricles into the portion of the VT zone covered by the overlap zone, when IMD 16 tracks native atrial pulses into the VT zone.

Following either a single sensed ventricular events (or multiple sensed ventricular events) while IMD 16 is performing pacing in the VT zone, e.g., above 150 bpm, IMD 16 may automatically switch the detection and pacing zones in a manner to remove overlap between the pacing and the VT detection zones. In addition, in some examples, IMD 16 may also apply a rate smoothing algorithm to prevent a sudden change in heart rate. IMD 16 may therefore leave the VT zone unobscured by ventricular pacing when these criteria are satisfied. Accordingly, IMD 16 may perform ventricular tracking up to 170 bpm during ventricular tracking or spontaneous atrial rhythms. During a dual chamber pacing mode, IMD 16 may perform pacing up to a maximum rate corresponding to the upper sensor rate, e.g., 140 bpm. During atrial paced ventricular sensed mode, IMD 16 may set the upper pacing rate equal to the upper sensing rate, e.g., 140 bpm.

IMD 16 may pace the ventricles into the VT zone when IMD 16 tracks native atrial pulses into the VT zone and perform rhythm discrimination while pacing in the overlap portion of the VT zone. When IMD 16 determines that heart 12 is operating in the VT zone and outside of the overlapping zone, IMD 16 may deliver a therapy designed to stop VT, e.g., one or more therapeutic doses of electric current for cardioversion or other anti-tachycardia therapy. Accordingly, when IMD 16 is tracking either a sinus tachycardia or atrial tachycardia, functionally IMD 16 may behave as if the upper pacing rate of the pacing zone is 170 beats per minute, as opposed to the example defined upper pacing rate for the pacing zone of 140 beats per minute. Thus IMD 16 may continue to pace one or both ventricles up to 170 beats per minute, when IMD 16 is tracking a sinus tachycardia or atrial tachycardia, for example. In this manner, IMD 16 may deliver ventricular pacing, including cardiac resynchronization, even during rapid heart rates when IMD 16 determines that the rapid heart rate is supraventricular tachycardia.

IMD 16 may further detect and treat ventricular tachycardias that occur during ventricular pacing within the overlap zone. In response to a sensed ventricular event (or events) within the overlap zone, IMD 16 may automatically switch programmed parameters such that IMD 16 stops delivering ventricular pacing above the pacing zone and instead delivers a therapy appropriate for ventricular tachycardia. In this manner, IMD 16 may determine whether a detected ventricular depolarization in the overlap zone is due to ventricular tachycardia or supraventricular tachycardia, and respond to each differently—to the supraventricular tachycardia by resetting the maximum ventricular rate and continuing pace the ventricles in the VT zone, if indicated by the atrial rate, and to the ventricular tachycardia by delivering a therapy to treat ventricular tachycardia, such as cardioversion.

When IMD 16 detects ventricular depolarizations of heart 12 in the overlap zone, IMD 16 may apply rhythm discriminators to determine whether the ventricular depolarization is VT or SVT, such as a sinus tachycardia or other 1:1 SVT. When IMD 16 determines that the ventricular depolarization is due to VT, IMD 16 may apply anti-tachycardia therapies. When IMD 16 determines that the ventricular depolarization is due to SVT while the rate is in the overlap zone, IMD 16 may apply overlap zone pacing. IMD 16 may apply traditional rhythm discriminators to determine whether VT has initiated. When IMD 16 determines that the rhythm is still SVT (for example, if the sensed ventricular events comprise one or more premature ventricular contractions (PVCs)), then IMD 16 may reinstate overlap zone pacing.

In some examples, programmer 24 comprises a handheld computing device, computer workstation, or networked computing device. Programmer 24 includes a user interface that receives input from a user and presents information to the user. A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD. For example, the user may define the pacing zone, the VT zone, the VF zone, the maximum tracking rate and the overlap zone using programmer 24 and download these zone definitions to IMD 16.

The user may use programmer 24 to retrieve information from IMD 16 regarding whether and when IMD 16 operated each zone or a time spent in each zone. For example, programmer 24 may retrieve data corresponding to whether IMD 16 determined that heart 12 had entered the VT zone, the overlap zone, and/or the VF zone. Programmer 24 may also retrieve data corresponding to an amount of time spent in each zone that was entered, such as a time spent in the overlap zone, a time spent in the VT zone, and a time spent in the VF zone. Programmer 24 may further retrieve data corresponding to a treatment delivered while in the overlap zone, e.g., data relating to whether pacing therapy or anti-tachycardia therapy was delivered.

IMD 16 and programmer 24 may communicate via wireless communication using any techniques known in the art. In some examples, IMD 16 may include a response module that sends an alert to, e.g., programmer 24 when IMD 16 detects a problem with heart 12 or other organs or systems of patient 14. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

In one example, data regarding the various zones detected by IMD 16 (such as a time spent in each zone and a therapy delivered while in the zone) is presented, potentially along with other sensed data, such as data indicating the status of heart failure in the patient. A user may utilize this data, for example, to determine effectiveness of a stimulation therapy administered to patient 14, e.g., by IMD 16, or a change in the status of patient 14. The user may also utilize the data to modify the therapy, e.g., modify one or more boundaries of one or more of the zones.

IMD 16 may provide several advantages. For example, IMD 16 may deliver pacing therapy to either or both of RV 28 and/or LV 32, even which such pacing causes RV 28 and/or LV 32 to enter the VT zone, when IMD 16 tracks the atria into the VT zone. This may be beneficial because, although RV 28 and/or LV 32 may be paced in the VT zone, this pacing may cause the ventricular contractions to be efficient. IMD 16 may also resynchronize spontaneous ventricular events that are not ventricular tachycardia or ventricular fibrillation. IMD 16 may therefore treat a patient undergoing resynchronization therapy and improve the efficiency of a fast ventricular rate, contrary to conventional devices that would stop pacing therapy when the heart rhythm is in the VT zone or even treat for anti-tachycardia despite the tachycardia being an SVT. IMD 16 may further provide an advantage for patients who suffer from a short diastolic filling period, i.e., incomplete ventricular filling, because IMD 16 may improve the efficiency of ventricular contraction when the heart rhythm is in the overlap zone portion of the VT zone as a result of SVT.

Contrary to conventional IMDs programmed so that a sensor response does not overlap with the VT zone, IMD 16 may be programmed such that the upper sensor rate applies to the paced atrial rates and perform ventricular tracking at rates greater than the upper sensor rate. Conventional IMDs and ICDs do not allow for overlapping zones for ventricular tachycardia detection and therapy and ventricular pacing. However, the techniques of this disclosure recognize that, in some settings, the ability to achieve these overlapping zones is desirable, e.g., because patient 14 may have relatively slow VTs that require treatment.

An IMD, such as IMD 16, programmed with overlapping zones may be particularly useful for patients who are physically active, e.g., during exercise. When IMD 16 comprises an ICD implanted within an active patient, IMD 16 may provide particular advantages over conventional devices. Studies have shown that for active patients with ICDs, resynchronization of spontaneous ventricular events may be ideal, regardless of rate (assuming the ventricular events are not VT or VF). For example, during periods of atrial fibrillation, flutter, or sinus tachycardia, there will be ventricular events that conventional ICDs do not resynchronize because the rate is above the maximum or upper tracking rate. While a clinician for an active patient with an ICD will likely control ventricular rates through adjustment of medication, the clinician may be compelled to ensure that the benefits of resynchronization are applied to such ventricular events. Accordingly, the clinician may utilize an IMD configured according to the techniques of this disclosure to ensure that, if the ventricular rate is going to be fast, the IMD may at least make sure that those beats are as efficient as the IMD can make them.

Figure 2:
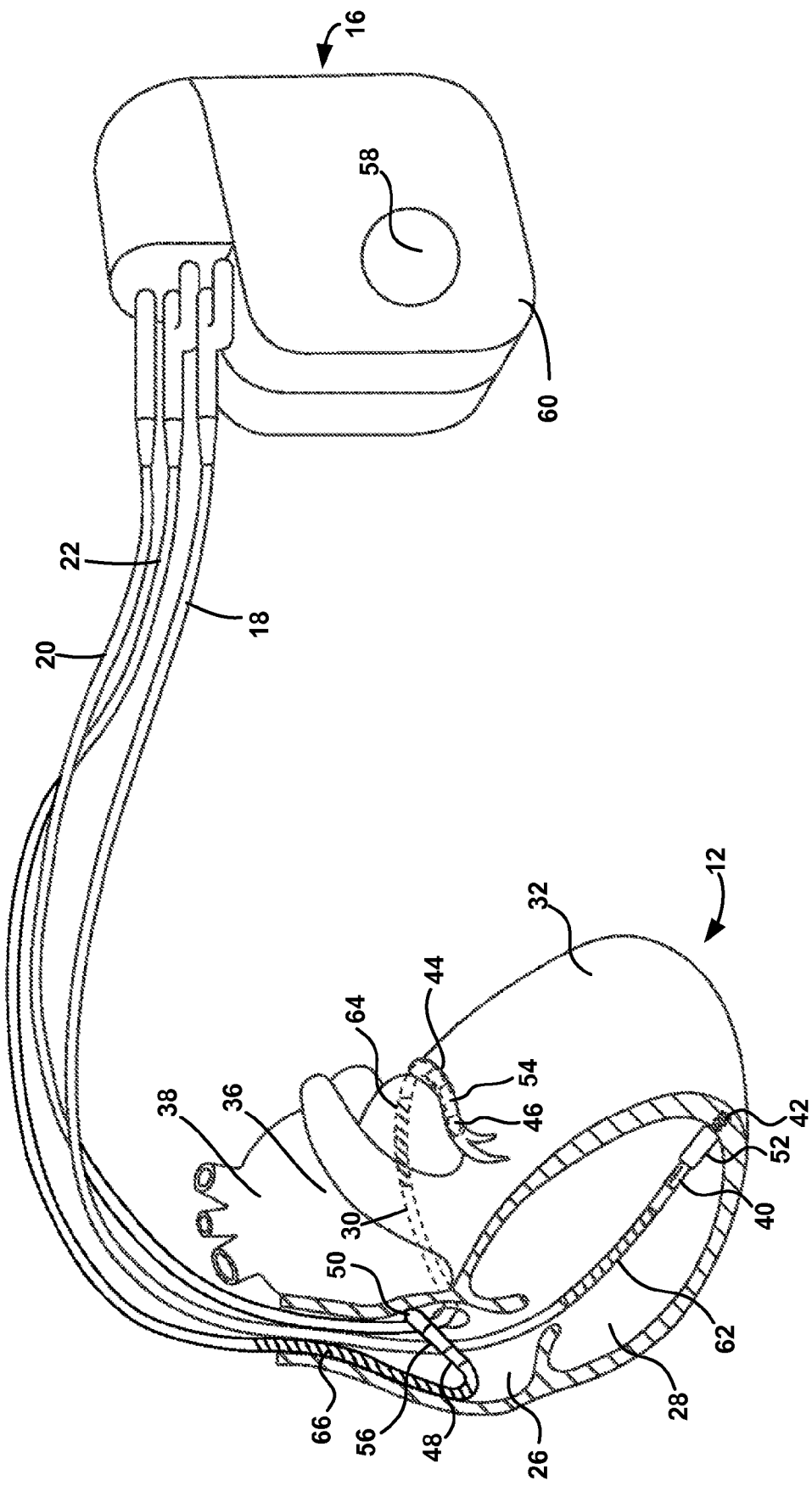
FIG. 2 is a conceptual diagram illustrating the example implantable medical device (IMD) and leads of the therapy system of FIG. 1 in greater detail.

FIG. 2 is a conceptual diagram illustrating IMD 16 and leads 18, 20, 22 of therapy system 10 in greater detail. Leads 18, 20, 22 include conductors that are electrically coupled to a stimulation generator and a sensing module (FIG. 4) within a housing 60 of IMD 16. The conductors are coupled to electrodes on the leads.

Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. Leads 18, 20, 22 also include elongated electrodes 62, 64, 66, respectively, which may take the form of a coil. There are no electrodes located in left atrium 36, but other examples may include electrodes in left atrium 36. Furthermore, other examples may include electrodes in other locations, such as the aorta or a vena cava, or epicardial or extracardial electrodes proximate to any of the chambers or vessels described herein. Each of the electrodes 40, 42, 44, 46, 48, 50, 62, 64, and 66 may be electrically coupled to a respective conductor within the lead body of its associated lead 18, 20, 22, and thereby coupled to the stimulation generator and sensing module within housing 60 of IMD 16.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. Housing electrode 58 is also coupled to one or both of the stimulation generator and sensing module within housing 60 of IMD 16.

IMD 16 senses electrical signals attendant to the depolarization and repolarization of heart 12 via any combination of electrodes 40, 42, 44, 46, 48, 50, 58, 62, 64, and 66. The electrical signals are conducted to IMD 16 from the electrodes via the respective leads 18, 20, 22 or, in the case of housing electrode 58, a conductor coupled to housing electrode 58. IMD 16 may sense such electrical signals via any bipolar combination of electrodes 40, 42, 44, 46, 48, 50, 58, 62, 64, and 66. Furthermore, any of the electrodes 40, 42, 44, 46, 48, 50, 58, 62, 64, and 66 may be used for unipolar sensing in combination with housing electrode 58.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver pacing pulses to heart 12 via any combination of elongated electrodes 62, 64, 66, and housing electrode 58. Electrodes 58, 62, 64, 66 may also be used to deliver cardioversion or defibrillation pulses to heart 12.

Any combination of electrodes 40, 42, 44, 46, 48, 50, 60, 62, 64 and 66 may be used for detecting a heart rhythm of heart 12 of patient 14 and delivering a pacing therapy, anti-tachycardia therapy, and/or defibrillation therapy in accordance with the techniques of this disclosure. In some examples, a first set of electrodes is selected to monitor one or both atria, and a second set of electrodes is selected to deliver a pacing pulse while the heart rhythm is in the pacing zone or in the overlap zone as a result of SVT. In this manner, IMD 16 may track one or both atria and pace either or both ventricles, even when the atria enter the VT zone. Other sets of electrodes may be selected to, e.g., deliver cardioversion in response to ventricular tachycardia or fibrillation.

The configuration of therapy system 10 illustrated in FIGS. 1 and 2 is merely one example. It should be understood that various other electrode and lead configurations for determining a heart rhythm zone and delivering a therapy based on the determined zone, especially where one zone comprises an overlapping zone, are within the scope of this disclosure. For example, a therapy system may include epicardial leads and/or patch electrodes instead of or in addition to transvenous leads 18, 20, 22 illustrated in FIG. 1. Further, IMD 16 need not be implanted within patient 14. For examples in which IMD 16 is not implanted in patient 14, IMD 16 may deliver pacing pulses and other therapies to heart 12 via percutaneous leads that extend through the skin of patient 14 to a variety of positions within or outside of heart 12.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. As another example, other examples of therapy systems may include a single lead that extends from IMD 16 into right ventricle 28, or two leads that respectively extend into the right ventricle 26 and proximate to the left ventricle 32. Another example of an alternate two-lead therapy system is shown in FIG. 3.

Figure 3:
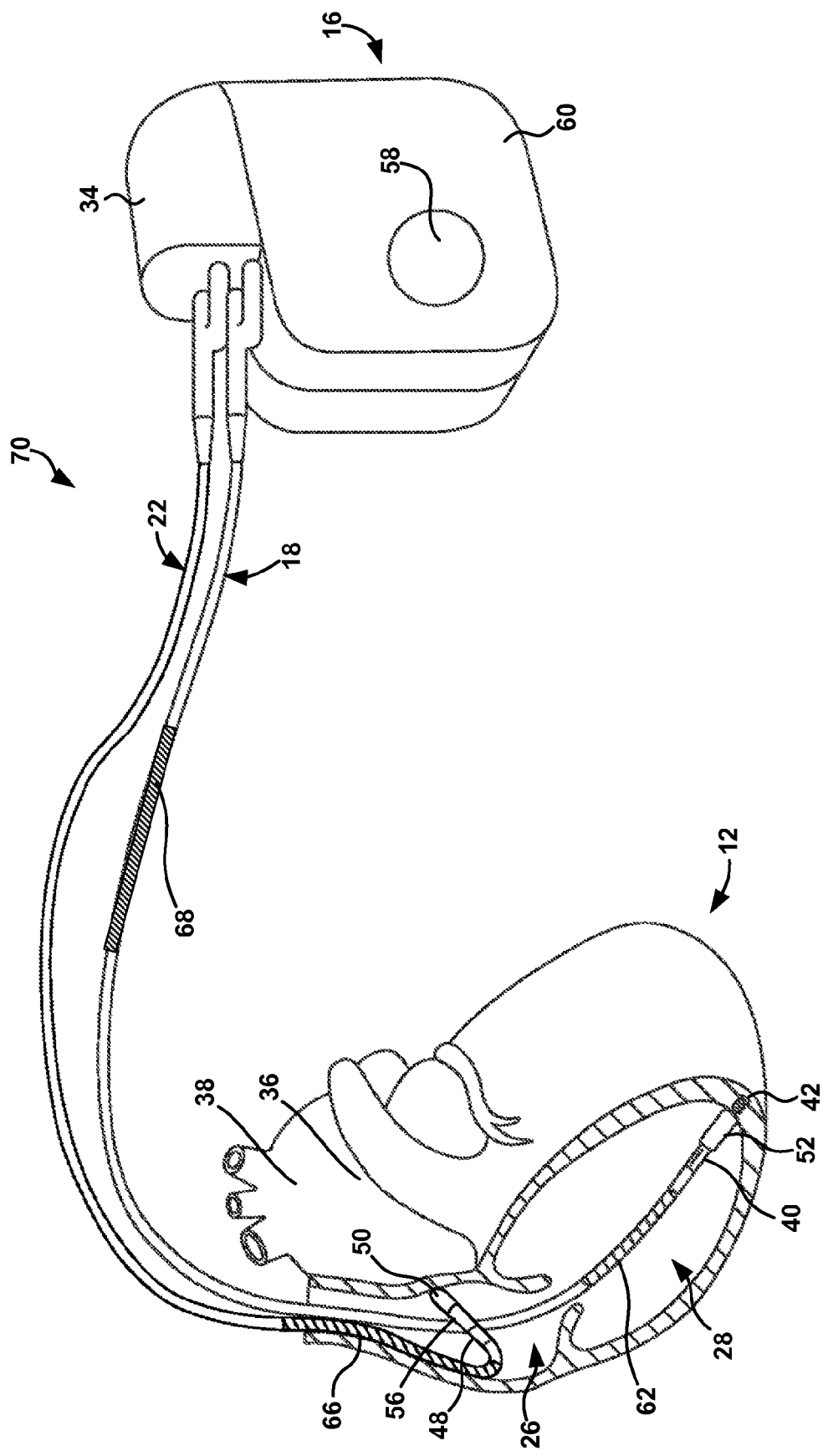
FIG. 3 is a conceptual diagram illustrating another example of a therapy system that is similar to the therapy system of FIGS. 1 and 2, but includes two leads rather than three leads.

FIG. 3 is a conceptual diagram illustrating another example of therapy system 70, which is similar to therapy system 10 of FIGS. 1-2, but includes two leads 18, 22, rather than three leads. Leads 18, 22 are implanted within right ventricle 28 and right atrium 26, respectively. Additionally, lead 18 includes electrode 68, which may take the form of a coil, as in the example of FIG. 3. Therapy system 70 shown in FIG. 3 may also be useful for providing pacing pulses to heart 12. System 70 may also be configured to operate in an overlap zone and to determine a therapy to provide in the overlap zone. In one example, system 70 may be configured such that system 70 continues to pace the ventricles into the VT zone while tracking the atria into the VT zone. In this manner, system 70 may continue to pace the ventricles even when system 70 determines that a rhythm for heart 12 will be between 150 bpm and 170 bpm. In some examples, system 70 determines whether a spontaneous ventricular event is caused by ventricular tachycardia or supraventricular tachycardia. System 70 may deliver a pacing therapy when system 70 determines that the spontaneous ventricular event is due to SVT and a cardioversion therapy when system 70 determines that the spontaneous ventricular event is due to VT.

Figure 4:
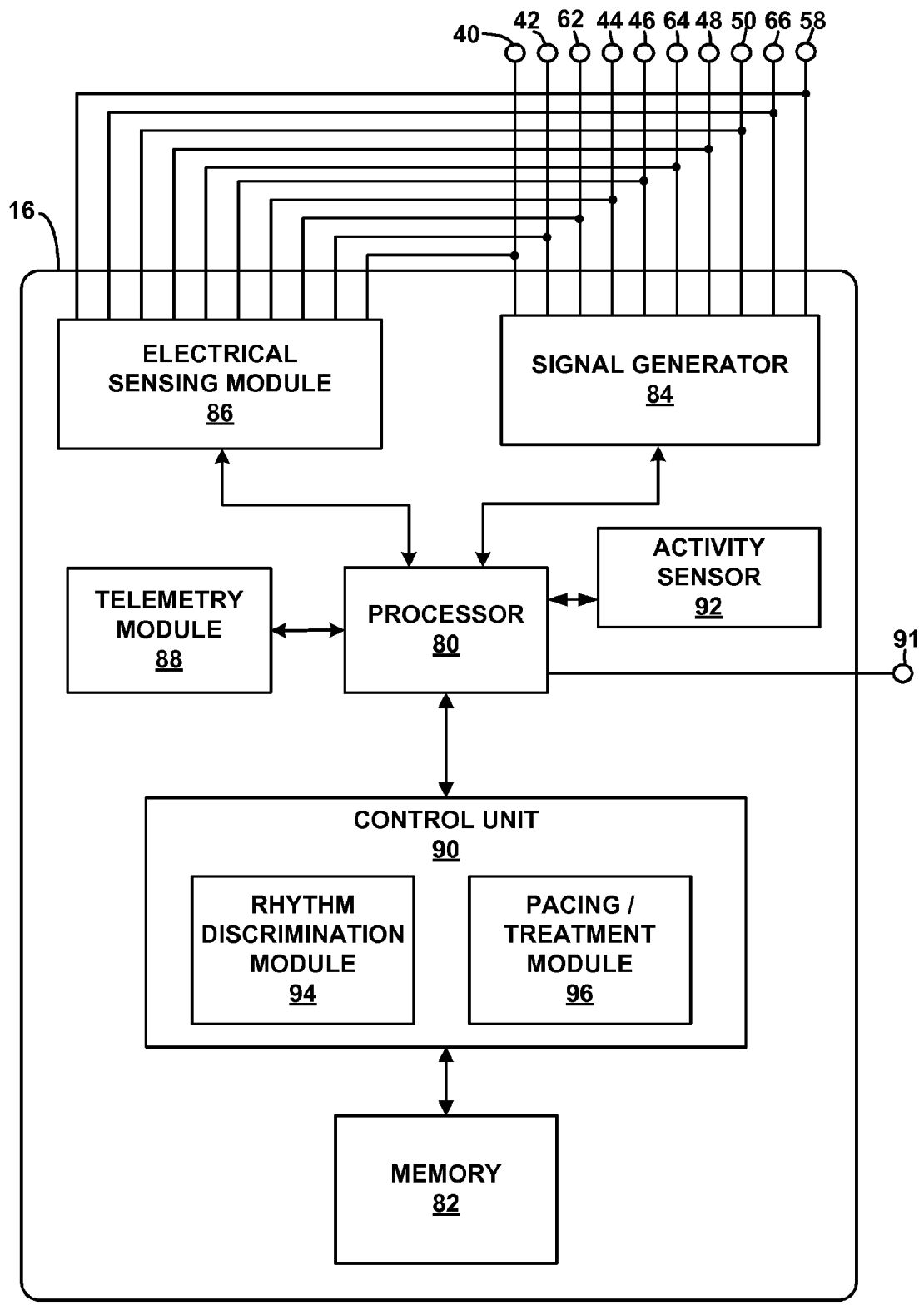
FIG. 4 is a block diagram illustrating one example configuration of an IMD.

FIG. 4 is a block diagram illustrating one example configuration of IMD 16. In the example illustrated by FIG. 4, IMD 16 includes a processor 80, memory 82, signal generator 84, electrical sensing module 86, hemodynamic sensor 91, activity sensor 92, and telemetry module 88. IMD 16 further includes control unit 90, which itself includes rhythm discrimination module 94 and pacing/treatment module 96. Pacing/treatment module 96 may also be referred to as a therapy module. Memory 82 may include, e.g., be encoded with, computer-readable instructions that, when executed by processor 80, cause IMD 16 and processor 80 to perform various functions attributed to IMD 16, processor 80, or control unit 90 herein. The computer-readable instructions may be encoded within memory 82. Memory 82 may comprise any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 and/or control unit 90 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 and/or control unit 90 may include multiple components, such as any combination of one or more microprocessors, one or more controllers, one or more DSPs, one or more ASICs, or one or more FPGAs, as well as other discrete or integrated logic circuitry. The functions attributed to processor 80 and/or control unit 90 herein may be embodied as software, firmware, hardware or any combination thereof. In one example, control unit 90, rhythm discrimination module 94, and pacing/treatment module 96 may be stored or encoded as instructions in memory 82 that are executed by processor 80. Additionally, any processor of any device described herein may implement one or more of control unit 90, rhythm discrimination module 94, and pacing/treatment module 96.

Processor 80 controls signal generator 84 to deliver stimulation therapy, e.g., cardiac pacing or CRT, to heart 12 according to a selected one or more therapy programs, which may be stored in memory 82. Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Signal generator 84 is configured to generate and deliver electrical stimulation therapy to heart 12 via selected combinations of electrodes 40, 42, 44, 46, 48, 50, 58, 62, 64, and 66. In some examples, signal generator 84 is configured to delivery cardiac pacing pulses. In other examples, signal generator 84 may deliver pacing or other types of stimulation in the form of other signals, such as sine waves, square waves, or other substantially continuous time signals.

Stimulation generator 84 may include a switch module and processor 80 may use the switch module to select, e.g., via a data/address bus, which of the available electrodes are used to deliver pacing pulses. Processor 80 may also control which of electrodes 40, 42, 44, 46, 48, 50, 58, 62, 64 and 66 is coupled to signal generator 84 for generating stimulus pulses, e.g., via the switch module. The switch module may include a switch array, switch matrix, multiplexer, or any other type of switching device suitable to selectively couple a signal to selected electrodes.

Electrical sensing module 86 monitors signals from at least one of electrodes 40, 42, 44, 46, 48, 50, 58, 62, 64 or 66 in order to monitor electrical activity of heart 12. Electrical sensing module 86 may also include a switch module to select which of the available electrodes are used to sense the cardiac activity. In some examples, processor 80 selects the electrodes that function as sense electrodes, or the sensing configuration, via the switch module within electrical sensing module 86.

Electrical sensing module 86 includes multiple detection channels, each of which may be selectively coupled to respective combinations of electrodes 40, 42, 44, 46, 48, 50, 58, 62, 64 or 66 to detect electrical activity of a particular chamber of heart 12. Each detection channel may comprise an amplifier that outputs an indication to processor 80 in response to detection of an event, such as a depolarization, in the respective chamber of heart 12. In this manner, processor 80 may detect the occurrence of R-waves and P-waves in the various chambers of heart 12.

Memory 82 stores intervals, counters, or other data used by processor 80 to control the delivery of pacing pulses by signal generator 84. Such data may include intervals and counters used by processor 80 to control the delivery pacing pulses to one or both of the left and right ventricles for CRT. The intervals and/or counters are, in some examples, used by processor 80 to control the timing of delivery of pacing pulses relative to an intrinsic or paced event, e.g., in another chamber. The counters may be set based on an A-A, V-V, A-V, A-RV, A-LV, or RV-LV interval, as examples.

In one example, rhythm discrimination module 94 uses electrical sensing module 86 to determine a rhythm of heart 12 of patient 14. For example, rhythm discrimination module 94 may calculate a number of beats per minute of heart 12 and determine one of a plurality of zones for the heart rhythm. Rhythm discrimination module 94 may interact with electrical sensing module 86 to receive indications of intrinsic depolarizations of the atria or ventricles to calculate the heart rhythm of heart 12. Rhythm discrimination module 94 may further retrieve zone definitions from memory 82 to determine a zone for the heart rhythm. In one example, memory 82 stores definitions for a pacing zone, a VT zone, a VF zone, and an overlap zone. In one example, the definition of the pacing zone may include heart rhythms between 60 bpm and 140 bpm, the VT zone may include heart rhythms between 150 bpm and 188 bpm, the VF zone may include heart rhythms above 188 bpm, and the overlap zone may include heart rhythms between 150 bpm and 170 bpm.

Rhythm discrimination module 94 may, when the heart rhythm is in the overlap zone, and a spontaneous ventricular depolarization is detected, determine a cause for the spontaneous ventricular depolarization. That is, rhythm discrimination module 94 may determine whether the spontaneous ventricular depolarization was due to a ventricular tachycardia or due to a supraventricular tachycardia, e.g., a natural response of either or both ventricles to an intrinsic atrial pulse. Rhythm discrimination module 94 may receive signals indicative of atrial and ventricular depolarizations from electrical sensing module 86 to determine whether the spontaneous ventricular depolarization occurred due to VT or SVT, using techniques known in the art.

Pacing/treatment module 96 selects and delivers a therapy to heart 12 based on the determination made by rhythm discrimination module 94. For example, when rhythm discrimination module 94 determines that intrinsic atrial pulses are occurring in the overlap zone portion of the VT zone, pacing/treatment module 96 may pace the ventricles into the VT zone. Moreover, if rhythm discrimination module 94 detects spontaneous ventricular depolarizations while signal generator 84 is delivering pacing pulses in the VT zone, rhythm discrimination module 94 may determine the origin of the intrinsic ventricular depolarizations, and pacing/treatment module 96 may select a treatment to apply based on the determination by the rhythm discrimination module 94. Pacing/treatment module 96 may continue to deliver pacing therapy while tracking the atria into the VT, adjust a timing interval between a sensed atrial event and a delivered ventricular pulse (e.g., according to the method described with respect to FIG. 9, below), or to deliver a cardioversion therapy, such as anti-tachycardia or defibrillation. Memory 82 may also store treatment definitions for each zone that define, for example, a pacing rate, a voltage, a current, a timing pattern, or other characteristics of therapeutic electrical doses to deliver to heart 12. Pacing/treatment module 96 may retrieve the treatment definitions from memory 82 and cause signal generator 84 to deliver the defined treatment via selected combinations of electrodes 40, 42, 44, 46, 48, 50, 58, 62, 64, and/or 66.

For example, when rhythm discrimination module 94 indicates that the heart rhythm is in the pacing zone, pacing/treatment module 96 may deliver a pacing therapy to heart 12. When rhythm discrimination module 94 indicates that the atria are entering the overlap portion of the VT zone, pacing/treatment module 96 may continue to deliver pacing pulses to the one or both ventricles based on sensed depolarizations atria, despite this pacing causing the ventricles to enter the VT zone. In this manner, IMD 16 may functionally behave as if the upper pacing rate was 170 bpm (i.e., as if the pacing zone included heart rhythms below 170 bpm) and the VT zone was 170 bpm to 188 bpm. When rhythm discrimination module 94 indicates that a detected spontaneous ventricular depolarization was VT, pacing/treatment module 96 may deliver a cardioversion (e.g., anti-tachycardia) therapy to heart 12. When rhythm discrimination module 94 indicates that a detected spontaneous depolarization was SVT, pacing/treatment module 96 may continue to deliver pacing therapy, and in some cases, may adjust one or more intervals between sensed atrial events and delivered ventricular pulses. When rhythm discrimination module 94 indicates that the heart rhythm is in the VF zone, pacing/treatment module 96 may deliver a defibrillation therapy.

Processor 80 and/or control unit 90 control the selection of electrode configurations for delivering pacing pulses and cardioversion therapy. In some examples, either or both of processor 80 or control unit 90 may implement the functions attributed to pacing/treatment module 96. For example, processor 80 may execute instructions of memory 82 for pacing/treatment module 96. Thus processor 80 may, in some examples, execute pacing/treatment module 96. Similarly, control unit 90 may implement or execute pacing/treatment module 96. Pacing/treatment module 96 may also interact with processor 80 to deliver pacing or cardioversion therapies to heart 12. Processor 80, for example, may communicate with signal generator 84 to select two or more stimulation electrodes in order to generate one or more pacing pulses for delivery to a selected chamber of heart 12, or to deliver a therapeutic dose of electric current for cardioversion or defibrillation therapy to heart 12. Processor 80 may also communicate with electrical sensing module 86 to select two or more sensing electrodes for detecting a rhythm of heart 12. Processor 80 may convey indications from electrical sensing module 86 to rhythm discrimination module 96 for analysis of the rhythm of heart 12.

In some examples, an existing IMD may receive a software, firmware, or hardware upgrade to implement the techniques of this disclosure. For example, an existing ICD may receive a software upgrade that includes instructions corresponding to rhythm discrimination module 94 and pacing/therapy module 96. The ICD may store rhythm discrimination module 94 and pacing/therapy module 96 as instructions in a memory or other computer-readable medium. In this manner, the computer-readable medium of the ICD may be encoded with instructions for rhythm discrimination module 94 and pacing/therapy module 96. A processor, control unit, or other hardware device of the ICD may execute the instructions to perform the techniques of this disclosure to determine whether a pacing therapy or a cardioversion therapy is appropriate in an overlap zone, e.g., heart rhythms between 150 bpm and 170 bpm. Likewise, the hardware device of the ICD may pace ventricles of a patient's heart into the VT zone when the ICD is tracking the atria into the VT zone, in accordance with the techniques of this disclosure.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide data to be uplinked to programmer 24 and receive data from programmer 24 via telemetry module 88.

In the example of FIG. 4, IMD 16 includes a hemodynamic sensor 91 and an activity sensor 92. In some examples, IMD 16 need not include one or both of hemodynamic sensor 91 and activity sensor 92. In some examples, IMD 16 may include more than one hemodynamic sensor 91 or activity sensor 92.

Hemodynamic sensor 91 may comprise one or more blood pressure of flow sensors, as examples. Activity sensor 92 may comprise, for example, one or more accelerometers. In some examples, the signal(s) generated by activity sensor may vary as a function of the posture, as well as the activity, of patient 14. In some examples, hemodynamic sensor 91 is located on one of leads 18, 20, and 22, or another lead, within the heart or vasculature of patient. In some examples, activity sensor 92 is located on or within the housing of IMD 16. In some examples, one or both of hemodynamic sensor 91 and activity sensor 92 provide an indication of patient demand for rate responsive pacing.

In some examples, pacing/treatment module 96 is configured to modify the maximum or upper ventricular tracking rate based on input from hemodynamic sensor 91. For example, pacing/treatment module 96 may determines the amount or rate by which to reduce the upper tracking rate after a sensed ventricular event during pacing in the overlap zone based on input from hemodynamic sensor 91, which may indicate the hemodynamic stability of the ventricular rhythm, for example. In some examples, pacing/treatment module 96 waits a period of time after a sensed ventricular event before dropping the upper tracking rate. The period of time may be determined based on input from hemodynamic sensor 91.

In some examples, pacing/treatment module 96 is configured to modify the maximum tracking rate (that is, an upper tracking rate) of the overlap zone when pacing into the VT zone according to signals received from activity sensor 92. For example, pacing/treatment module 96 may set the upper tracking rate of the overlap zone higher when activity sensor 92 indicates that the activity level associated with patient 14 is higher, and pacing/treatment module 96 may set the upper tracking rate of the overlap zone lower when activity sensor 92 indicates that the activity level associated with patient 14 is lower. In this manner, pacing/treatment module 96 may modify the upper tracking rate of the overlap zone according to an activity level of patient 14.

Figure 5:
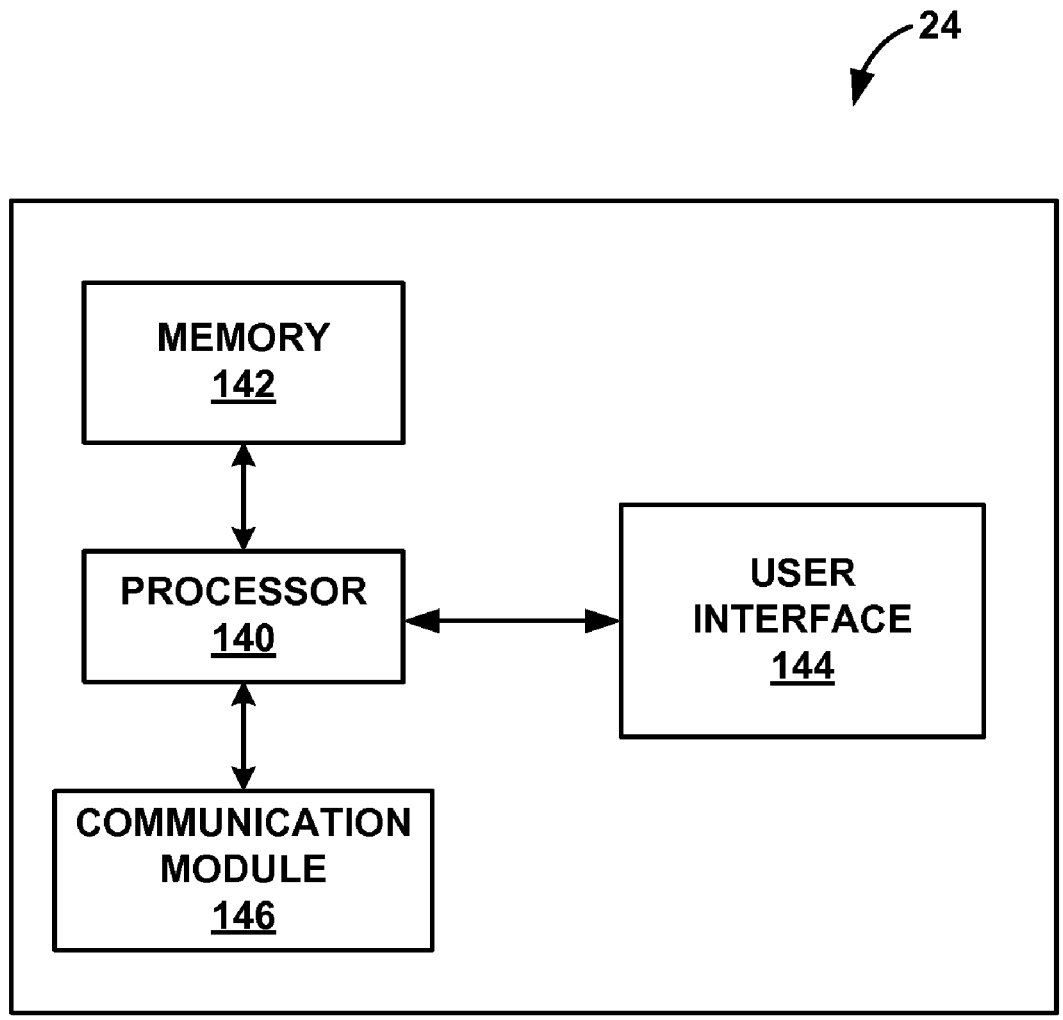
FIG. 5 is block diagram illustrating an example configuration of a programmer for programming an IMD.

FIG. 5 is block diagram illustrating an example configuration of programmer 24. In general, a programmer may be a computing device. In the example shown in FIG. 5, programmer 24 includes a processor 140, memory 142, user interface 144, and communication module 146. Programmer 24 may comprise a dedicated hardware device with dedicated software for programming of IMD 16. Alternatively, programmer 24 may comprise an off-the-shelf computing device running an application that enables programmer 24 to program IMD 16. For example, programmer 24 may comprise a workstation computer, a laptop computer, a hand-held device such as a personal digital assistant (PDA), a cellular phone or smart phone, or other devices.

A clinician or other user interacts with programmer 24 via user interface 144, which may include a display to present a graphical user interface to a user, and a keypad, mouse, light pen, stylus, microphone for voice recognition, or other mechanism(s) for receiving input from a user. In some examples, processor 140 retrieves historical data 102 from IMD 16 via communication module 146, and controls user interface 144 to present graphical and/or textual representations of the data.

Processor 140 can take the form of one or more microprocessors, DSPs, ASICs, FPGAs, programmable logic circuitry, or the like, and the functions attributed to processor 140 herein may be embodied as hardware, firmware, software or any combination thereof. Memory 142 may store instructions that cause processor 140 to provide the functionality ascribed to programmer 24 herein, and information used by processor 140 to provide the functionality ascribed to programmer 24 herein. Additionally, processor 140 may perform the functionality of any or all of control unit 90, rhythm discrimination module 94, or pacing/treatment module 96 described with respect to FIG. 4. Moreover, memory 142 may be encoded with instructions to cause processor 140 to update software or firmware of IMD 16 to perform the techniques of this disclosure. In this manner, memory 142 may comprise instructions for performing the techniques of this disclosure either to cause processor 140 to perform the techniques, or so that processor 140 can upload the instructions to IMD 16 via communications module 146.

Memory 142 may include any fixed or removable magnetic, optical, or electrical media, such as RAM, ROM, CD-ROM, hard or floppy magnetic disks, EEPROM, flash memory, or the like. Memory 142 may also include a removable memory portion that may be used to provide memory updates or increases in memory capacities. A removable memory may also allow patient data to be easily transferred to another computing device, or to be removed before programmer 24 is used to program therapy for another patient. Memory 142 may also store information that controls therapy delivery by IMD 16, such as stimulation parameter values.

Programmer 24 may communicate wirelessly with IMD 16, such as by using RF communication or proximal inductive interaction. This wireless communication is possible through the use of communication module 146, which may be coupled to an internal antenna or an external antenna (not shown). Communication module 142 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16. An example of such an arrangement is discussed with respect to FIG. 6.

Processor 140 of programmer 24 may implement any of the techniques described herein, or otherwise perform any of the methods described below. For example, processor 140 of programmer 24 may calculate a heart rhythm zone for a patient. Processor 140 may cause a device to deliver pacing therapy in the VT zone when tracking intrinsic atrial pulses into the VT zone. Processor 140 may also, upon determining that the heart rhythm zone comprises an overlap zone (e.g., 150 bpm to 170 bpm), further determine an origin of a spontaneous ventricular depolarization, which may include either ventricular tachycardia or supraventricular tachycardia. Upon determining that the origin was supraventricular tachycardia, processor 140 may instruct the device, e.g., via communication module 146, to deliver a pacing therapy, and potentially modify the pacing therapy being delivered. Upon determining that the origin was ventricular tachycardia, processor 140 may instruct the device to deliver a cardioversion or other anti-tachycardia therapy. The device may comprise an implantable or external medical device. Processor 140 may implement one or more of control unit 90, rhythm discrimination module 94, and pacing/treatment module 96.

Rather than issuing instructions, or in addition to issuing the instructions, processor 140 may instruct user interface 144 to display an indication (e.g., a graphical or textual representation) of the current heart rhythm zone, an origin of a spontaneous ventricular depolarization when the spontaneous ventricular depolarization occurs in an overlap zone, and a recommended or delivered therapy. Similarly, processor 140 may store data in memory 142 corresponding to the detected heart rhythm zone, an origin of a spontaneous ventricular depolarization, and a recommended or delivered therapy.

Figure 6:
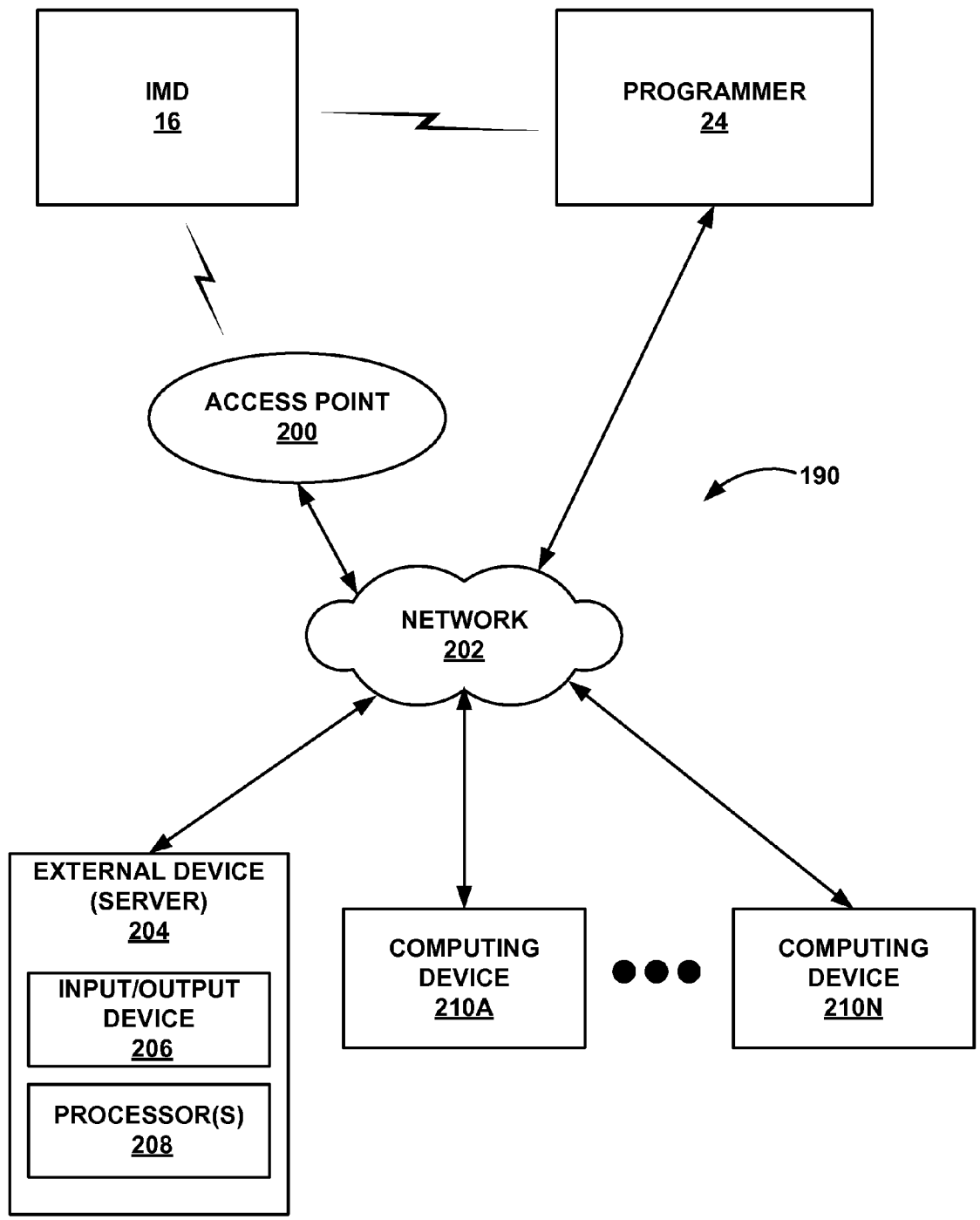
FIG. 6 is a block diagram illustrating an example system that includes a server and one or more computing devices that are coupled to the IMD and the programmer shown in FIG. 1 via a network.

FIG. 6 is a block diagram illustrating an example system 190 that includes an external device, such as a server 204, and one or more computing devices 210A-210N (computing devices 210), that are coupled to IMD 16 and programmer 24 shown in FIG. 1 via a network 202. In this example, IMD 16 may use its telemetry module 88 to communicate with programmer 24 via a first wireless connection, and to communication with an access point 200 via a second wireless connection. In the example of FIG. 6, access point 200, programmer 24, server 204, and computing devices 210 are interconnected, and able to communicate with each other, through network 202. In some cases, one or more of access point 200, programmer 24, server 204, and computing devices 210 may be coupled to network 202 through one or more wireless connections. IMD 16, programmer 24, server 204, and computing devices 210 may each comprise one or more processors, such as one or more microprocessors, DSPs, ASICs, FPGAs, programmable logic circuitry, or the like, that may perform various functions and operations, such as those described herein.

Access point 200 may comprise a device that connects to network 186 via any of a variety of connections, such as telephone dial-up, digital subscriber line (DSL), fiber optic, wireless, or cable modem connections. In other examples, access point 200 may be coupled to network 202 through different forms of connections, including wired or wireless connections. In some examples, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16.

In some examples, access point 200, server 204, or computing devices 210 may perform any of the various functions or operations described herein. For example, processor 208 of server 204 may determine a zone within which a heart rhythm of a patient is. Processor 208 may track intrinsic atrial pulses into the VT zone and control IMD 16 to continue to deliver pacing therapy to the ventricles, despite such therapy causing the ventricles to enter the VT zone, when tracking intrinsic atrial pulses. Processor 208 may also, upon determining that a spontaneous ventricular depolarization occurred in an overlap zone (e.g., 150 bpm to 170 bpm), further determine an origin of the spontaneous ventricular depolarization, such as either ventricular tachycardia or supraventricular tachycardia. Upon determining that the origin was supraventricular tachycardia, processor 208 may instruct IMD 16 via network 202 to continue to deliver a pacing therapy and/or to modify the pacing therapy, e.g., by modifying an A-V interval. Upon determining that the origin was ventricular tachycardia, processor 208 may instruct IMD 16 to deliver a cardioversion therapy, anti-tachycardia pacing therapy, or any other anti-tachycardia therapy. In some examples, any or all of programmer 24, access point 200, server 204, or computing devices 210 may perform some or all of the actions described herein. In some examples, any or all of programmer 24, access point 200, server 204, or computing devices 210 may implement one or more of control unit 90, rhythm discrimination module 94, and pacing/treatment module 96.

In some cases, server 204 may be configured to provide a secure storage site for data that has been collected from IMD 16 and/or programmer 24. Network 202 may comprise a local area network, wide area network, or global network, such as the Internet. In some cases, programmer 24 or server 204 may assemble data in web pages or other documents for viewing by and trained professionals, such as clinicians, or by the patient, via viewing terminals associated with computing devices 210. Server 204 may also display the web pages or documents using input/output device 206. Processor 208 may also generate statistics regarding a frequency of entry into various heart rhythm/operational zones, a duration of time spent in each zone, an average time spent in each zone, a heart rhythm zone entered following treatment for a patient whose heart rhythm enters a VT or VF zone, a number of times that SVT is determined as the origin of a spontaneous ventricular depolarization, a number of times that VT is determined as the origin of a spontaneous ventricular depolarization, or other statistics or measurements. The illustrated system of FIG. 6 may be implemented, in some aspects, with general network technology and functionality similar to that provided by the Medtronic CareLink® Network developed by Medtronic, Inc., of Minneapolis, Minn.

In one example, a user, such as a clinician, surgeon, physician, or other user, may adjusting a lead, or an electrode of a lead, for IMD 16 within patient 14, after reviewing output presented by programmer 24, server 204, computing devices 210, or other device in communication with IMD 16. The user may also program IMD 16 to use a different combination of electrodes to deliver pacing pulses. The user may also define or redefine the heart rhythm zones, such as the overlap zone, to cause IMD 16 to deliver or determine various therapies for each of the heart rhythm zones.

Figure 7:
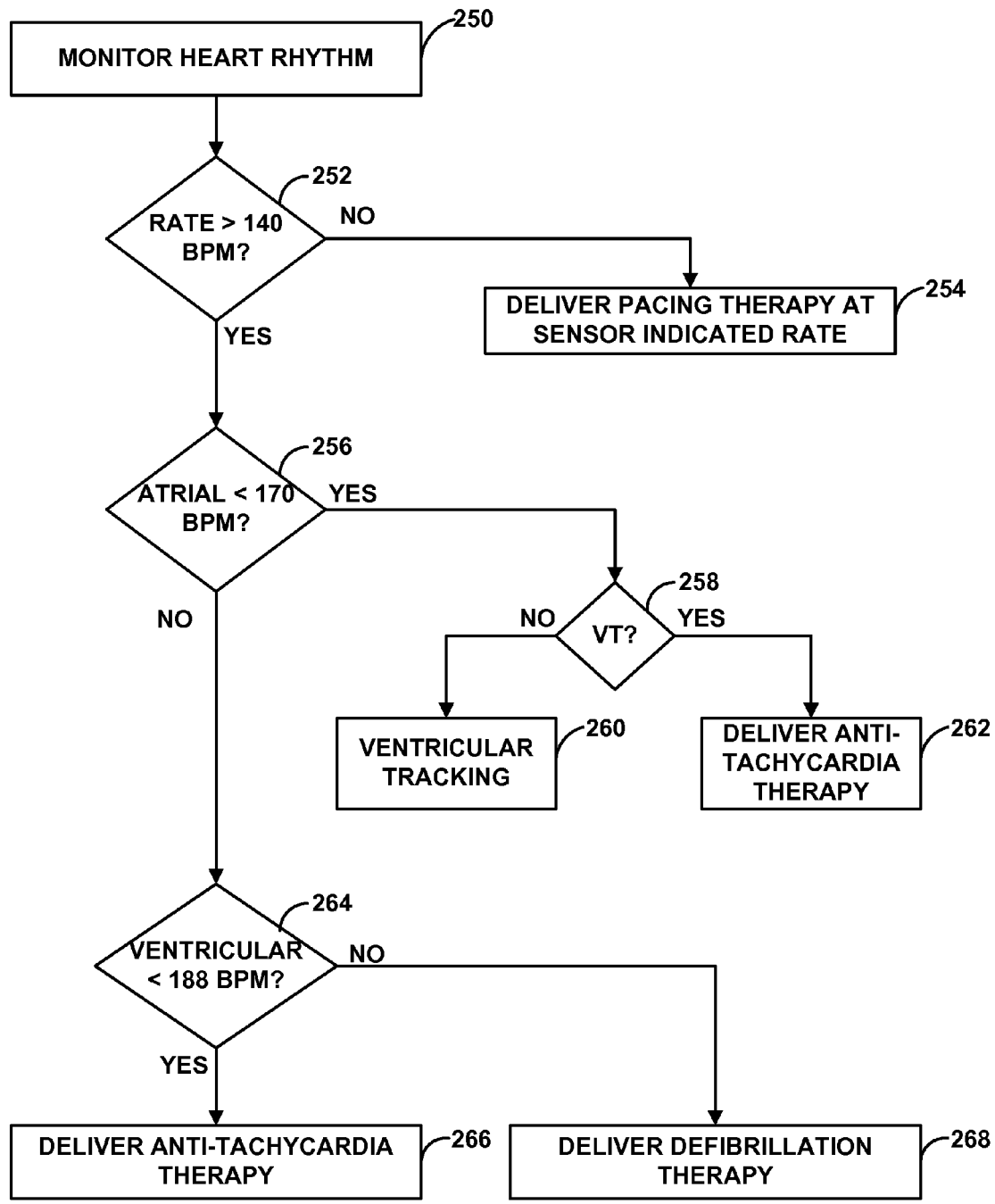
FIG. 7 is a flowchart illustrating an example method for delivering a therapy to a patient based on a heart rhythm zone determined for the patient.

FIG. 7 is a flowchart illustrating an example method for delivering a therapy to a patient based on a zone within which a heart rhythm of the patient is. The method includes, when pacing within an overlap zone, determining an origin for a spontaneous ventricular depolarization, and continuing to deliver pacing therapy when the origin comprises supraventricular tachycardia. Although described with respect to IMD 16, it should be understood, as described above, that other devices, such as internal or external devices, may implement some or all of the example method of FIG. 7.

Initially, IMD 16 monitors the rhythm of heart 12 of patient 14 (250). IMD 16 may monitor for intrinsic depolarizations and determine rates in one or more chambers of heart using any of various known techniques. IMD 16 then generally determines a heart rhythm zone for the calculated heart rhythm, e.g., one of a pacing zone, an overlap zone, a VT zone, or a VF zone. In the example method of FIG. 7, IMD 16 determines whether the heart rhythm is in the pacing zone, e.g., whether there is an intrinsic heart rhythm greater than 140 bpm (252). When the heart rhythm is in the pacing zone ("NO" branch of 252), IMD 16 delivers a pacing therapy to one or both of the atria or ventricles at the sensor indicated rate according to techniques and pacing modes known in the art (254).

When IMD 16 determines that there is rhythm above the pacing zone ("YES" branch of 252), IMD 16 determines whether the intrinsic atrial rate is in the overlap zone by determining whether the rate is less than a maximum tracking rate, e.g., 170 bpm in the example of FIG. 7 (256). When IMD 16 determines that the atrial rate is in the overlap zone ("YES" branch of 256), IMD 16 monitors for ventricular tachycardia (258) by monitoring for intrinsic ventricular depolarizations. So long as no VT (or VF) is detected, IMD 16 delivers ventricular tracking pacing to one or both ventricles based on the intrinsic rate of the atria (260). IMD 16 monitors for VT during ventricular tracking pacing. If IMD 16 detects an intrinsic ventricular depolarization, IMD 16 may apply rhythm discriminators to determine whether the rhythm is VT or sinus tachycardia (or other 1:1 SVT). IMD 16 may apply the rhythm discriminators, for example, when P-R rhythms (atrial sensed, ventricular sensed) are occurring in the overlap zone to determine if the episode is SVT or VT.

When IMD 16 determines that the origin is supraventricular tachycardia ("NO" branch of 258), IMD 16 continues to deliver ventricular tracking pacing therapy to heart 12 (260). In this manner, IMD 16 may functionally behave as if the upper pacing rate were at the upper limit of the overlap zone, e.g., 170 bpm, and that the VT zone comprises only 170 bpm to 188 bpm. Thus, IMD 16 may continue to deliver pacing therapy to the ventricles, even when such pacing therapy causes the ventricles to enter the VT zone, assuming that IMD 16 has tracked the atria into the VT zone. IMD 16 may thereby perform ventricular pacing (including cardiac resynchronization) even during rapid heart rates, e.g., heart rates between 140 bpm and 170 bpm. When IMD 16 determines that the origin is ventricular tachycardia ("YES" branch of 258), IMD 16 delivers an anti-tachycardia therapy, such as cardioversion (262). In this manner, IMD 16 may deliver the anti-tachycardia therapy in the overlap zone in response to a sensed ventricular event (or events), thereby treating the VT zone as comprising 150 bpm to 188 bpm. Functionally, IMD 16 may extend the VT zone to include 150 bpm to 188 bpm. IMD 16 may select the therapy to apply according to traditional VT detection criteria.

In some examples, when IMD 16 senses ventricular events during the period of overlap ventricular pacing, IMD 16 may suspend the overlap programming or modify the programming such that ventricular pacing ceases, and IMD 16 may apply rhythm discriminators to determine if VT has initiated. If IMD 16 determines that the rhythm is still SVT, for example, or if the sensed ventricular events comprised one or more PVCs, then IMD 16 may reinitiate overlap pacing behavior.

In some examples, IMD 16 performs a search AV function within the overlap zone to determine whether intrinsic AV conduction occurs at the calculated heart rate. In one example, IMD 16 senses native atrial beats (P) that are followed by ventricular paced beats (V) in the overlap zone. IMD 16 may allow the AV interval to gradually increase until an intrinsic ventricular beat (R) occurs. IMD 16 may first determine that AV conduction is present in the overlap zone, then respond according to pre-programmed settings, such as resuming ventricular pacing at the programmed AV interval. Effectively, IMD 16 may thereby resynchronize ventricular contraction during supraventricular tachycardia.

In one example, IMD 16 may detect a "dropped" ventricular beat, from which IMD 16 may determine that spontaneous AV conduction is not occurring in the overlap zone. IMD 16 may respond according to pre-programmed parameters, such as lowering the upper tracking rate to 140 bpm, allowing occasional AV block, so that the ventricular rate is no more than 140 bpm. Such ventricular pacing below the intrinsic atrial rate may provide rate smoothing for the ventricles during intermittent AV conduction. In this manner, IMD 16 may avoid unnecessary pacing in the overlap zone for CRT patients, while assuring that if ventricular activity does occur through native AV conduction, IMD 16 will resynchronize the ventricular activity.

When IMD 16 determines, however, that the intrinsic atrial rate is not in the overlap zone ("NO" branch of 256), IMD 16 determines whether the intrinsic ventricular rate is in the VT zone or the VF zone (264). In the example method of FIG. 7, IMD 16 determines that the ventricular rate is in the VT zone when the heart rhythm is below 188 bpm and in the VF zone when the heart rhythm is above 188 bpm. When IMD 16 determines that the ventricular rate is in the VT zone ("YES" branch of 264), IMD 16 delivers an anti-tachycardia therapy (266). When IMD 16 determines that the ventricular rate is in the VF zone ("NO" branch of 264), IMD 16 delivers a defibrillation therapy (268). In addition to rate, IMD 16 may detect or confirm ventricular fibrillation using morphological or other techniques known in the art.

Figure 8:
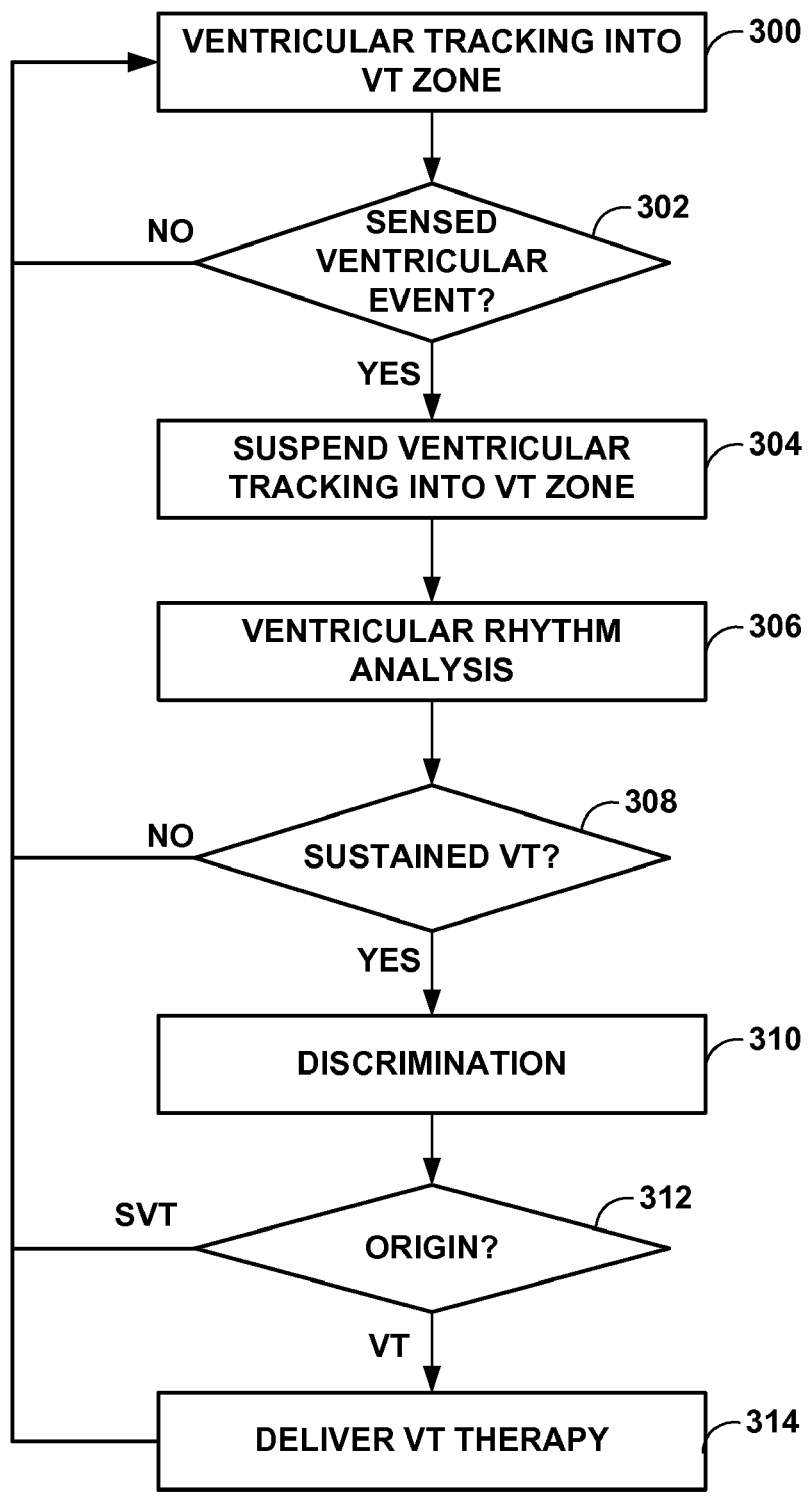
FIG. 8 is a flowchart illustrating an example method for delivering ventricular tracking pacing at rates within a ventricular tachycardia zone.

FIG. 8 is a flowchart illustrating an example method for delivering ventricular tracking pacing at rates within a ventricular tachycardia zone. Although described with respect to IMD 16, it should be understood that any device equipped to deliver cardiac therapy, or any other device in communication with a device that delivers cardiac therapy, such as a programmer, server, or computing device described herein, may perform all or part the method of FIG. 8. Moreover, although the steps of FIG. 8 are shown sequentially, it should be understood that certain steps may occur in parallel, such as performing ventricular rhythm analysis and rhythm discrimination in parallel.

Initially, IMD 16 performs ventricular tracking into the VT zone (300). That is, as discussed above, IMD 16 tracks intrinsic atrial depolarizations that enter the VT zone and delivers pacing pulses to one or both of the ventricles according to intrinsic atrial pulses in the VT zone. IMD 16 also attempts to detect a ventricular event, such as a spontaneous ventricular depolarization (302). When IMD 16 does not detect a spontaneous ventricular event ("NO" branch of 302), IMD 16 continues to perform ventricular tracking in the VT zone.

When IMD 16 senses a ventricular event ("YES" branch of 302), IMD 16 suspends ventricular tracking in the VT zone (304) and performs ventricular rhythm analysis to determine an origin of the sensed ventricular event (306). Although IMD 16 suspends ventricular tracking in the VT zone in response to sensing a single ventricular event in the example of FIG. 8, in other examples, IMD 16 suspends ventricular tracking in the VT zone in response to detecting a threshold number of ventricular events, or a threshold number of ventricular events within a predetermined period of time or with less than a threshold interval between the events. In some examples, IMD 16 suspends ventricular tracking in the VT zone in response to sensing X ventricular events within the previous Y sensed or paced ventricular events.

When IMD 16 determines that the sensed ventricular event is not a sustained ventricular tachycardia ("NO" branch of

308), IMD 16 again performs ventricular tracking in the VT zone. IMD 16 may determine that a ventricular tachycardia is sustained when, for example, the ventricles spontaneously depolarize a certain number of consecutive or proximate times at a rate within the VT zone.

When IMD 16 determines that the ventricular tachycardia is sustained ("YES" branch of 308), IMD 16 applies rhythm discriminators (310) to determine an origin of the sustained ventricular tachycardia (312). The application of rhythm discriminators may include monitoring the intrinsic atrial rate in addition to the intrinsic ventricular rate to determine whether the ventricular rate is of supraventricular origin, e.g., a 1:1 SVT. When the origin is determined to be supraventricular tachycardia ("SVT" branch of 312), IMD 16 may continue to perform ventricular tracking in the VT zone. However, when IMD 16 determines that the origin of the sustained VT is ventricular tachycardia ("VT" branch of 312), IMD 16 delivers a ventricular tachycardia therapy, such as cardioversion or anti-tachycardia pacing.

Figure 9:
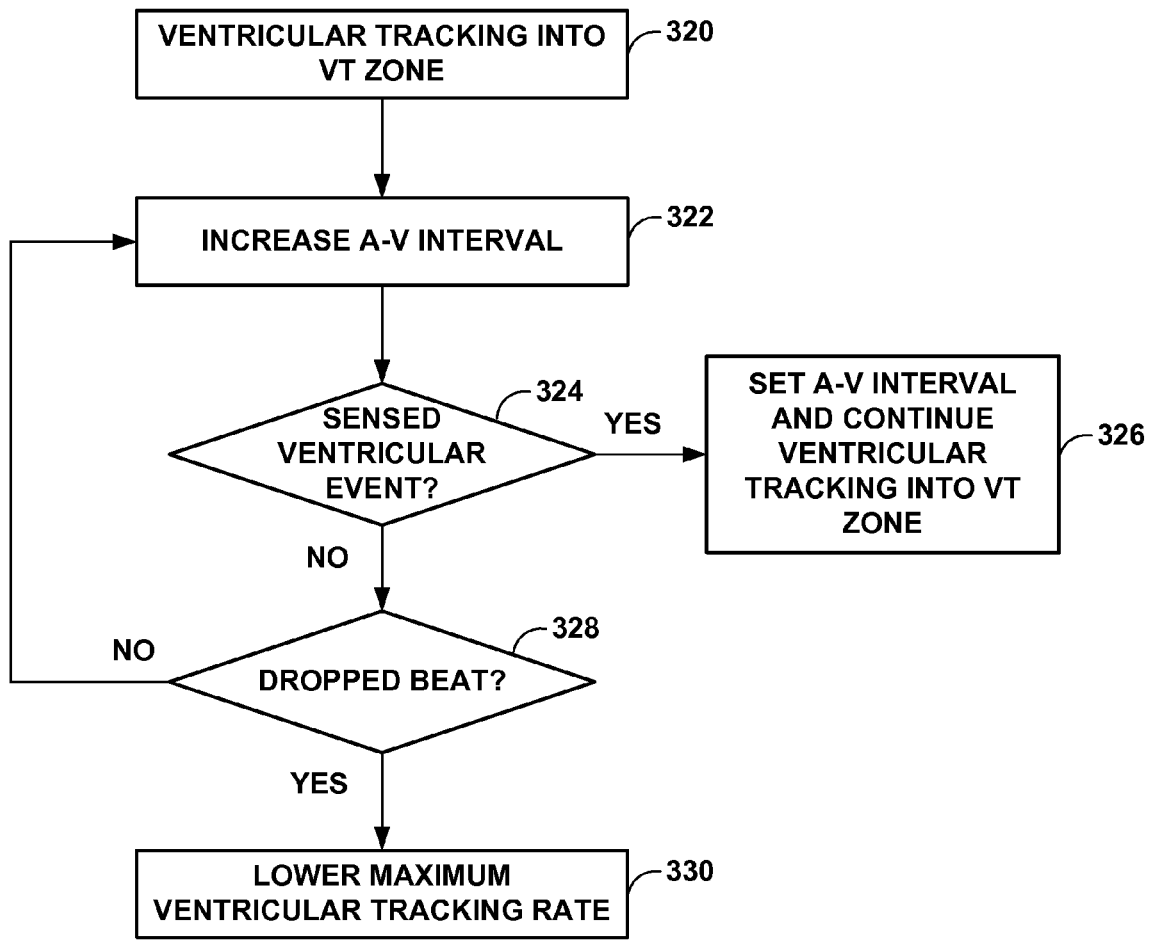
FIG. 9 is a flowchart illustrating an example method for determining whether to provide ventricular tracking pacing at rates within a ventricular tachycardia zone for a cardiac resynchronization therapy patient.

FIG. 9 is a flowchart illustrating an example method for determining whether to provide ventricular tracking pacing at rates within a ventricular tachycardia zone for a cardiac resynchronization therapy patient. The method of FIG. 9 may be used to determine the A-V interval for pacing in the VT zone. Although described with respect to IMD 16, it should be understood that any device equipped to perform cardiac resynchronization therapy, or any programmer, server, or computing device in communication with such a device, may perform all or part of the method of FIG. 9.

Initially, IMD 16 performs ventricular tracking into the VT zone (320). That is, as discussed above, IMD 16 tracks intrinsic atrial rates that enter the VT zone and delivers pacing pulses to one or both ventricles, as specified by the CRT for the patient, according to intrinsic atrial rate in the VT zone. IMD 16 then increases the A-V interval (322). As noted, the A-V interval generally comprises a time period between sensing an atrial event and delivering a ventricular pacing pulse. Accordingly, IMD 16 generally may deliver a ventricular pacing pulse following a time period corresponding to the A-V interval after sensing an atrial event so long as no intrinsic ventricular depolarization is detected during the A-V interval. Assuming that the initial A-V interval is X, IMD 16 may increase the A-V interval, e.g., to X=X+1. The A-V interval may be an A-RV or A-LV interval. In some cases, both an A-RV and A-LV interval may be increased.

IMD 16 may then attempt to detect a spontaneous ventricular event within the A-V interval (324). When no spontaneous ventricular contraction has been detected, IMD 16 determines whether a dropped ventricular beat has occurred, e.g., whether another atrial depolarization is detected prior to a ventricular depolarization or expiration of the A-V interval (328). So long as no sensed ventricular event during the A-V interval or dropped beat occurs, IMD 16 continues to increase the A-V interval (322). The A-V interval may be increased after each delivery of a ventricular pacing pulse upon expiration of the current A-V interval, or after a number N of such ventricular pacing pulse deliveries.

When IMD 16 senses a spontaneous ventricular event within the current A-V interval, IMD 16 sets the A-V interval and performs ventricular tracking pacing in the VT zone according to the A-V interval (326). Effectively, IMD 16 determines that it has resynchronized ventricular contraction during supraventricular tachycardia. In some examples, IMD 16 sets the A-V interval back to the preprogrammed interval, or may change the programmed A-V interval to the interval at which the intrinsic ventricular event was detected or another interval based on the interval at which the intrinsic ventricular event was detected.

When a dropped beat is detected (328), IMD 16 lowers the maximum ventricular tracking rate (330). For example, IMD 16 may lower the upper tracking rate to be equal to the upper bound of the pacing zone, e.g., 140 bpm, allowing the occasional A-V block. In this manner, the method of FIG. 9 may prevent unnecessary ventricular pacing in the overlap zone and provide ventricular rate smoothing, while potentially assuring that if ventricular activity does occur through native A-V conduction, that these events will be resynchronized.

Figure 10:
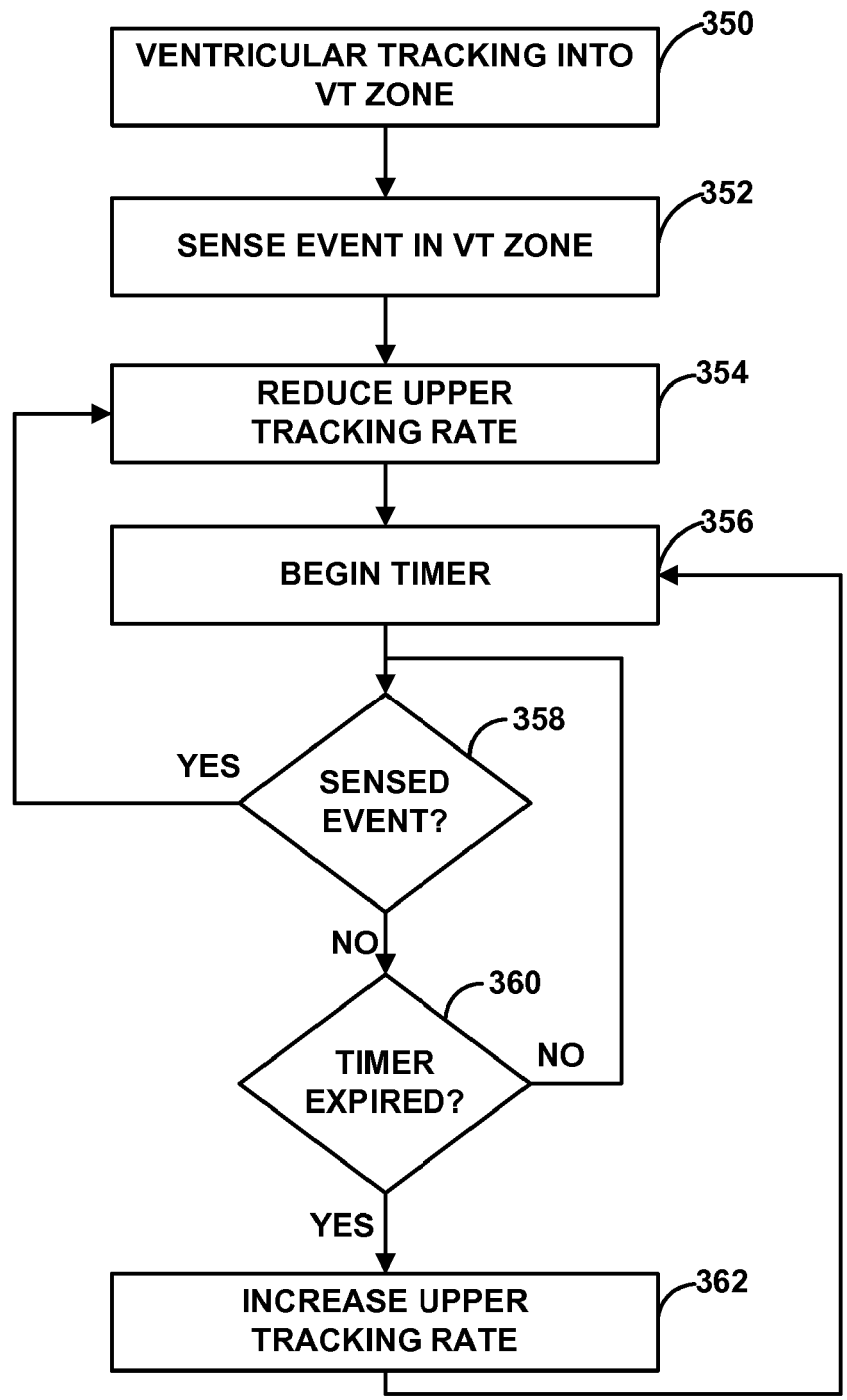
FIG. 10 is a flowchart illustrating an example method for varying an upper tracking rate based on continued sensing of ventricular events during ventricular tachycardia zone pacing.

FIG. 10 is a flowchart illustrating an example method for varying an upper tracking rate based on continued sensing of ventricular events during ventricular tachycardia zone tracking and pacing. FIG. 10 represents one example method for dynamically modifying the maximum tracking rate. Initially, IMD 16 performs ventricular tracking into the VT zone (350). That is, as discussed above, IMD 16 tracks intrinsic atrial rates that enter the VT zone and delivers pacing pulses to one or both ventricles according to intrinsic atrial rate in the VT zone.

While pacing in the VT zone, IMD 16 may sense a ventricular event, or a plurality of ventricular events meeting one or more criteria, as discussed above (352). When this occurs, IMD 16 may dynamically reduce the upper tracking rate, as discussed above (354). IMD 16 may then begin a timer (356) to determine a time period during which to leave the upper tracking rate reduced.

If IMD 16 senses an event before the timer has expired ("YES" branch of 358), IMD 16 may further reduce the upper tracking rate (354) and restart the timer (356). However, if the timer expires without IMD 16 sensing an event ("NO" branches of 358 and 360), IMD 16 may increase the upper tracking rate (362). In this manner, IMD 16 may dynamically adjust the upper tracking rate. More particularly, IMD 16 may dynamically modify the upper tracking rate by reducing the upper tracking rate following sensed ventricular events, and IMD 16 may further reverse the modification to the upper tracking rate when there are no sensed events for a particular period of time. In some examples, IMD 16 may perform a similar method, but rather than determining the level of the upper tracking rate, IMD 16 may determine a rate of change by which to reduce the upper tracking rate.

Figure 11:
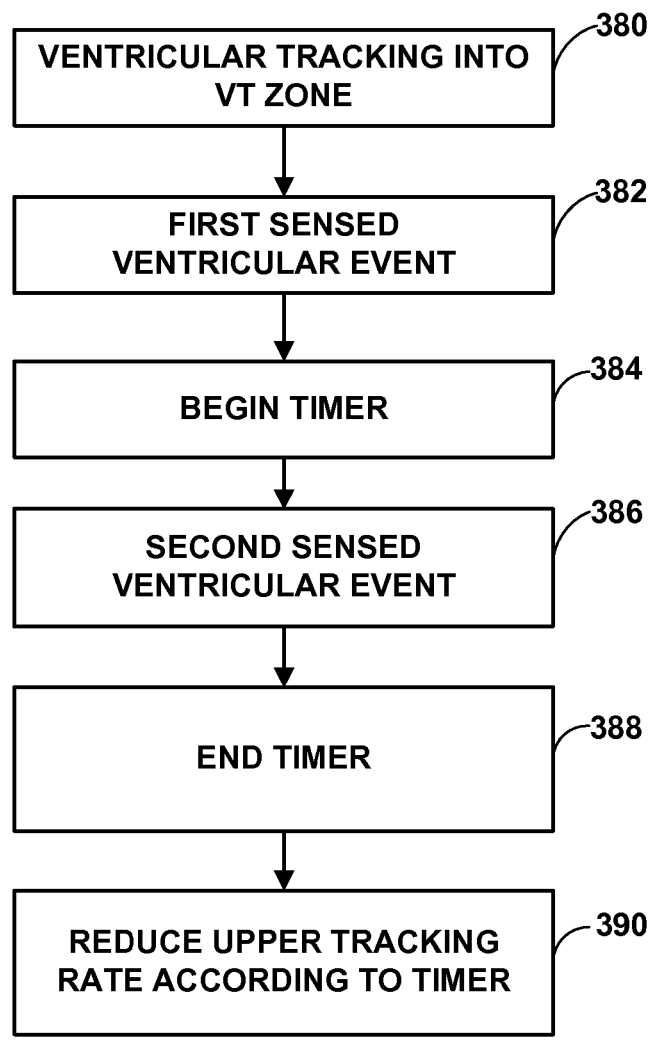
FIG. 11 is a flowchart illustrating an example method for varying the upper tracking rate based on a time interval between two consecutive sensed ventricular events.

FIG. 11 is a flowchart illustrating an example method for varying the upper tracking rate based on a time interval between two consecutive sensed ventricular events. FIG. 11 represents another example method for dynamically modifying the maximum tracking rate. Initially, IMD 16 performs ventricular tracking into the VT zone as discussed herein (380). After sensing a first ventricular event (382), IMD 16 begins a timer (384). Then after sensing a second ventricular event (386), which may comprise a consecutive event (an event in the beat following the beat in which the first event was sensed), IMD 16 may end the timer (388). IMD 16 may use the time interval between the first sensed event and the second sensed event, that is, the value of the timer, to reduce the upper tracking rate (390). In this manner, IMD 16 may dynamically modify the upper tracking rate based on the apparent intrinsic ventricular rate.

Figure 12:
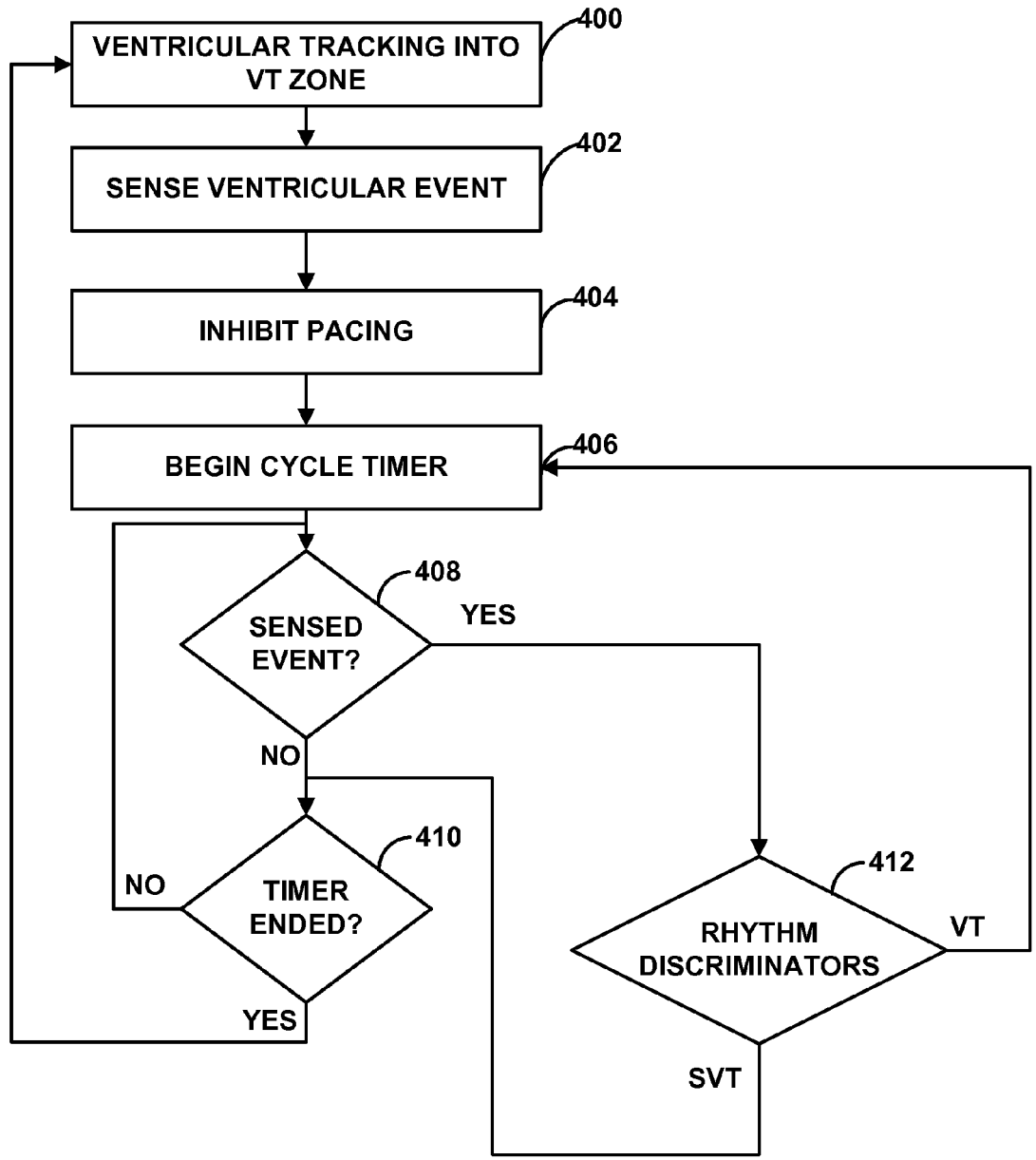
FIG. 12 is a flowchart illustrating an example method for modifying pacing in the VT zone after sensing one or more ventricular events.

FIG. 12 is a flowchart illustrating an example method for modifying pacing in the VT zone after sensing one or more ventricular events. Initially, IMD 16 performs ventricular tracking into the VT zone as discussed above (400). Upon sensing a ventricular event (402), IMD 16 may inhibit pacing (404) for a period of time.

In particular, IMD 16 may begin a cycle timer (406) after inhibiting pacing in response to a sensed event. If IMD 16 senses an event before expiration of the timer ("YES" branch of 408), IMD 16 may apply rhythm discriminators (412) to the sensed event. If the rhythm discriminators indicate that the event was VT, IMD 16 may continue to inhibit pacing for an additional cycle, e.g., by resetting the cycle timer (406). If the rhythm discriminators indicate that the event was SVT, however, IMD 16 may continue to wait for expiration of the cycle timer or until sensing another ventricular event. If the timer ends without a sensed event determined to comprise VT ("YES" branch of 410), IMD 16 may restart pacing in the VT zone.

Figure 13:
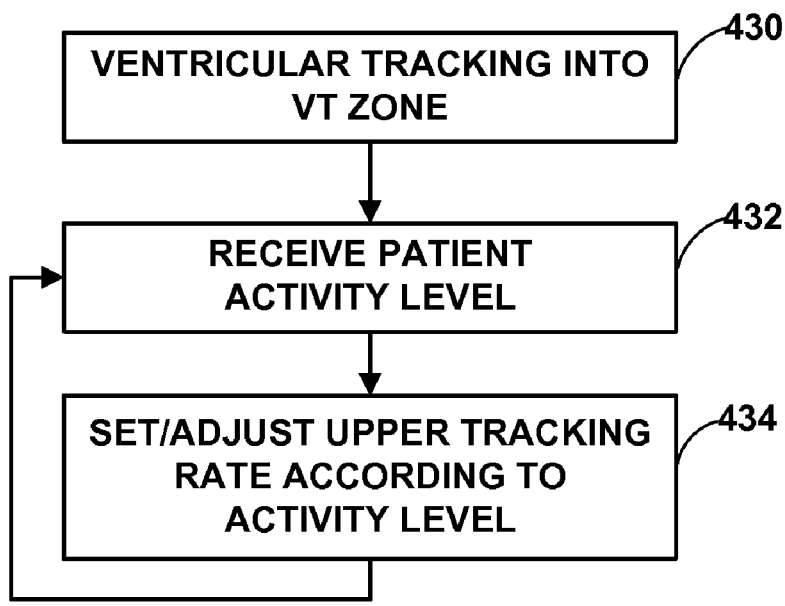
FIG. 13 is a flowchart illustrating an example method for varying the upper tracking rate based on an activity level of a patient.

FIG. 13 is a flowchart illustrating an example method for varying the upper tracking rate based on an activity level of a patient. FIG. 13 represents one example method for dynamically modifying the maximum tracking rate. Initially, IMD 16 performs ventricular tracking into the VT zone (430). That is, as discussed above, IMD 16 tracks intrinsic atrial rates that enter the VT zone and delivers pacing pulses to one or both ventricles, as specified by the CRT for the patient, according to intrinsic atrial rate in the VT zone. IMD 16 may then receive an indication of the patient's activity level (432), e.g., using activity sensor 92. IMD 16 may further determine the upper tracking rate according to the determined activity level (434). In some examples, IMD 16 may set the upper tracking rate only once according to the activity level, while in other examples, IMD 16 may periodically evaluate the activity level and modify the upper tracking rate according to changes in activity level.

The manner in which IMD 16 modifies the upper tracking rate using the activity level may comprise one or more programmable features. For example, IMD 16 may receive instructions from programmer 24 as to how to set the upper tracking rate. The instructions may establish the relationship between activity level and upper tracking rate according to one or more of an absolute upper tracking rate, an activity slope (how much to increase the upper tracking rate for each unit of change in the activity level), and activity threshold (an activity level above which IMD 16 may increase the upper tracking rate of the overlap zone, under which IMD 16 will not modify the upper tracking rate).

The techniques described in this disclosure may be implemented, at least in part, in hardware, software, firmware, or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

The invention claimed is:

1. A method comprising:
    storing a ventricular tachycardia zone, wherein the ventricular tachycardia zone specifies ventricular depolarization rates indicative of ventricular tachycardia;
    delivering ventricular tracking pacing at rates within the ventricular tachycardia zone, wherein delivering ventricular tracking pacing comprises delivering pacing pulses to at least one ventricle of a heart in response to detecting intrinsic atrial depolarizations at rates within the ventricular tachycardia zone;
    detecting an intrinsic ventricular depolarization during the delivery of ventricular tracking pacing; and
    in response to detecting the intrinsic ventricular depolarization, determining whether a ventricular tachycardia or supraventricular tachycardia is detected.

2. The method of claim 1, further comprising storing a maximum ventricular tracking rate that is greater than a lower bound of the ventricular tachycardia zone, wherein delivering ventricular tracking pacing comprises delivering pacing pulses to the ventricle at rates up to the maximum ventricular tracking rate.

3. The method of claim 2, wherein the maximum ventricular tracking rate comprises 170 beats per minute.

4. The method of claim 2, further comprising delivering an anti-tachycardia therapy to the heart in response to detecting intrinsic ventricular depolarizations at rates above the maximum ventricular tracking rate and within the ventricular tachycardia zone.

5. The method of claim 2, further comprising lowering the maximum ventricular tracking rate in response to sensing one or more ventricular events while delivering the ventricular tracking pacing within the ventricular tachycardia zone.

6. The method of claim 5, wherein lowering the maximum ventricular tracking rate comprises selecting at least one of a rate at which the maximum tracking rate is lowered or an amount by which the maximum ventricular tracking rate is lowered based on a number of the ventricular events that are sensed.

7. The method of claim 5, further comprising reversing the lowering of the maximum ventricular tracking rate after a predetermined period of time during which no ventricular events are sensed.

8. The method of claim 5, wherein lowering the maximum ventricular tracking rate comprises selecting at least one of a rate at which the maximum tracking rate is lowered or an amount by which the maximum ventricular tracking rate is lowered based on a time interval between two consecutive of the sensed ventricular events.

9. The method of claim 5, wherein lowering the maximum ventricular tracking rate comprises selecting at least one of a rate at which the maximum tracking rate is lowered or an amount by which the maximum ventricular tracking rate is lowered based on a signal from a hemodynamic sensor.

10. The method of claim 5, wherein lowering the maximum ventricular tracking rate comprises lowering the maximum ventricular tracking rate based on the morphology of the one or more sensed ventricular events.

11. The method of claim 2, further comprising selecting the maximum ventricular tracking rate based on a signal from a patient activity sensor.

12. The method of claim 1, further comprising suspending ventricular tracking pacing within the ventricular tachycardia zone upon detecting the intrinsic ventricular depolarization.

13. The method of claim 12, wherein suspending ventricular tracking pacing comprises reducing a maximum ventricular pacing rate below a lower bound of the ventricular tachycardia zone.

14. The method of claim 12, further comprising:
delivering a ventricular tachycardia therapy if a ventricular tachycardia is detected; and
resuming ventricular tracking pacing within the ventricular tachycardia zone if a supraventricular tachycardia is detected.

15. The method of claim 1, further comprising:
iteratively increasing an atrioventricular interval during the delivery of ventricular tracking pacing within the ventricular tachycardia zone;
when an intrinsic ventricular depolarization is detected during the iterative increasing of the atrioventricular interval during the delivery of ventricular tracking pacing within the ventricular tachycardia zone, setting the atrioventricular delay and continuing ventricular tracking pacing within the ventricular tachycardia zone based on the detection of the intrinsic ventricular depolarization during the iterative increasing of the atrioventricular interval; and
when a dropped ventricular beat is detected during the iterative increasing of the atrioventricular interval during the delivery of ventricular tracking pacing within the ventricular tachycardia zone, stopping ventricular tracking pacing within the ventricular tachycardia zone based on the detection of the dropped ventricular beat.

16. The method of claim 1, further comprising delivering at least one of cardioversion therapy and defibrillation therapy in response to a detected ventricular tachycardia.

17. A medical system comprising:
a memory that stores a ventricular tachycardia zone, wherein the ventricular tachycardia zone specifies ventricular depolarization rates indicative of ventricular tachycardia;
a medical device that detects intrinsic atrial depolarizations; and
a control unit that controls the medical device to deliver ventricular tracking pacing at rates within the ventricular tachycardia zone by delivering pacing pulses to at least one ventricle of a heart in response to the medical device detecting intrinsic atrial depolarizations at rates within the ventricular tachycardia zone,
wherein the medical device detects an intrinsic ventricular depolarization during the delivery of ventricular tracking pacing, and, in response to the medical device detecting the intrinsic ventricular depolarization, the control unit determines whether a ventricular tachycardia or supraventricular tachycardia is detected.

18. The system of claim 17, wherein the memory stores a maximum ventricular tracking rate that is greater than a lower bound of the ventricular tachycardia zone, and the control unit controls the medical device to deliver ventricular tracking pacing at rates up to the maximum ventricular tracking rate.

19. The system of claim 18, wherein the control unit controls the medical device to deliver an anti-tachycardia therapy to the heart in response to the medical device detecting intrinsic ventricular depolarizations at rates above the maximum ventricular tracking rate and within the ventricular tachycardia zone.

20. The system of claim 18, wherein the control unit lowers the maximum ventricular tracking rate in response to sensing one or more ventricular events while delivering the ventricular tracking pacing within the ventricular tachycardia zone.

21. The system of claim 20, wherein the control unit selects at least one of a rate at which the maximum tracking rate is lowered or an amount by which the maximum ventricular tracking rate is lowered based on a number of the ventricular events that are sensed.

22. The system of claim 20, wherein the control unit reverses the lowering of the maximum ventricular tracking rate after a predetermined period of time during which no ventricular events are sensed.

23. The system of claim 20, wherein the control unit selects at least one of a rate at which the maximum tracking rate is lowered or an amount by which the maximum ventricular tracking rate is lowered based on a time interval between two consecutive of the sensed ventricular events.

24. The system of claim 20, wherein the control unit selects at least one of a rate at which the maximum tracking rate is lowered or an amount by which the maximum ventricular tracking rate is lowered based on a signal from a hemodynamic sensor.

25. The system of claim 20, wherein the control unit lowers the maximum ventricular tracking rate based on the morphology of the one or more sensed ventricular events.

26. The system of claim 18, wherein the control unit selects the maximum ventricular tracking rate based on a signal from a patient activity sensor.

27. The system of claim 17, wherein the control unit suspends ventricular tracking pacing by the medical device within the ventricular tachycardia zone upon detecting the intrinsic ventricular depolarization.

28. The system of claim 27, wherein the control unit controls the medical device to deliver a ventricular tachycardia therapy when a ventricular tachycardia is detected, and resume ventricular tracking pacing within the ventricular tachycardia zone when a supraventricular tachycardia is detected.

29. The system of claim 17, wherein the control unit reduces a maximum ventricular pacing rate below a lower bound of the ventricular tachycardia zone upon detecting the intrinsic ventricular depolarization.

30. The system of claim 17, wherein the control unit:
iteratively increases an atrioventricular interval during the delivery of ventricular tracking pacing within the ventricular tachycardia zone by the medical device,
when an intrinsic ventricular depolarization is detected by the medical device during the iterative increasing of the atrioventricular interval during the delivery of ventricular tracking pacing within the ventricular tachycardia zone, sets the atrioventricular delay and controls the medical device to continue ventricular tracking pacing within the ventricular tachycardia zone based on the detection of the intrinsic ventricular depolarization during the iterative increasing of the atrioventricular interval, and when a dropped ventricular beat is detected by the medical device during the iterative increasing of the atrioventricular interval during the delivery of ventricular tracking pacing within the ventricular tachycardia zone, stops ventricular tracking pacing within the ventricular tachycardia zone by the medical device based on the detection of the dropped ventricular beat.

31. The system of claim 17, wherein the medical device comprises an implantable medical device.

32. The system of claim 17, wherein the medical device comprises the memory and the control unit.

33. The system of claim 17, wherein the control unit controls the medical device to deliver at least one of cardioversion therapy and defibrillation therapy when the control unit detects a ventricular tachycardia.

34. A computer-readable medium encoded with instructions for causing a programmable processor to:

store a ventricular tachycardia zone, wherein the ventricular tachycardia zone specifies ventricular depolarization rates indicative of ventricular tachycardia; and control a medical device to:

deliver ventricular tracking pacing at rates within the ventricular tachycardia zone, wherein the instructions that cause the programmable processor to control the medical device to provide ventricular tracking pacing comprise instructions that cause the programmable processor to control the medical device to deliver pacing pulses to at least one ventricle of a heart in response to detecting intrinsic atrial depolarizations at rates within the ventricular tachycardia zone;

detect an intrinsic ventricular depolarization during the delivery of ventricular tracking pacing; and in response to detection of the intrinsic ventricular depolarization, determine whether a ventricular tachycardia or supraventricular tachycardia is detected.

35. The computer-readable medium of claim 34, further comprising instructions for causing the programmable processor to control the medical device to deliver at least one of cardioversion therapy and defibrillation therapy in response to a detected ventricular tachycardia.

36. A medical system comprising:

means for storing a ventricular tachycardia zone, wherein the ventricular tachycardia zone specifies ventricular depolarization rates indicative of ventricular tachycardia;

means for delivering ventricular tracking pacing at rates within the ventricular tachycardia zone, wherein the means for delivering ventricular tracking pacing comprises means for delivering pacing pulses to at least one ventricle of a heart in response to detecting intrinsic atrial depolarizations at rates within the ventricular tachycardia zones;

means for detecting an intrinsic ventricular depolarization during the delivery of ventricular tracking pacing; and means for, in response to detecting the intrinsic ventricular depolarization, determining whether a ventricular tachycardia or supraventricular tachycardia is detected.

37. The medical system of claim 36, further comprising means for delivering at least one of cardioversion therapy and defibrillation therapy in response to a detected ventricular tachycardia.

* * * * *